US012635861B2

(12) United States Patent
Tavakkolmoghaddam et al.

(10) Patent No.: US 12,635,861 B2
(45) Date of Patent: May 26, 2026

(54) ATTACHMENT MECHANISM FOR USING AN ENDOSCOPE WITH A SURGICAL ROBOT

(71) Applicants: BOSTON SCIENTIFIC SCIMED, INC., Maple Grove, MN (US); WORCESTER POLYTECHNIC INSTITUTE, Worcester, MA (US)

(72) Inventors: Farid Tavakkolmoghaddam, Worcester, MA (US); Zhanyue Zhao, Shrewsbury, MA (US); Anne Gu, Brighton (UA); Avnish Sachar, Cambridge, MA (US); Christopher J. Nycz, Holden, MA (US); Bryan Allen Clark, Forest Lake, MN (US); Paris Marks Saint-Preux, Lowell, MA (US)

(73) Assignees: BOSTON SCIENTIFIC SCIMED, INC., Maple Grove, MN (US); WORCESTER POLYTECHNIC INSTITUTE, Worcester, MA (US)

( * ) Notice: Subject to any disclaimer, the term of this patent is extended or adjusted under 35 U.S.C. 154(b) by 451 days.

(21) Appl. No.: 18/201,534

(22) Filed: May 24, 2023

(65) Prior Publication Data

US 2023/0380670 A1    Nov. 30, 2023

Related U.S. Application Data

(60) Provisional application No. 63/345,532, filed on May 25, 2022.

(51) Int. Cl.
*A61B 1/00* (2006.01)
*A61B 34/00* (2016.01)
(Continued)

(52) U.S. Cl.
CPC .......... *A61B 1/0016* (2013.01); *A61B 1/0004* (2022.02); *A61B 1/0014* (2013.01);
(Continued)

(58) Field of Classification Search
CPC ... A61B 1/0004; A61B 1/0014; A61B 1/0016; A61B 1/00149
See application file for complete search history.

(56) References Cited

U.S. PATENT DOCUMENTS

| | | | |
|---|---|---|---|
| 4,461,282 A | 7/1984 | Ouchi et al. | |
| 5,578,052 A | 11/1996 | Koros et al. | |
(Continued)

FOREIGN PATENT DOCUMENTS

| | | | |
|---|---|---|---|
| CN | 104757930 A | 7/2015 | |
| CN | 111110989 A | 5/2020 | |
(Continued)

OTHER PUBLICATIONS

ASGE, "Minimizing Occupational Hazards in Endoscopy: Personal Protective Equipment, Radiation Safety, and Ergonomics," Gastro-intestinal Endoscopy Journal, vol. 72, No. 2, 9 pp. 227-235, 2010.
(Continued)

*Primary Examiner* — Aaron B Fairchild
(74) *Attorney, Agent, or Firm* — Seager, Tufte & Wickhem LLP

(57) ABSTRACT

A surgical system for use with a surgical robot may include an endoscope including a handle and an elongate shaft extending distally from the handle, an attachment mechanism including a fixture configured to receive the handle of the endoscope and a mounting structure configured to attach the fixture to the surgical robot, a motorized introducer apparatus spaced apart from the surgical robot and configured to translate the elongate shaft of the endoscope relative to a patient, and an input device configured to be operated (Continued)

using one hand only. The input device may include a plurality of tactile buttons operable using the one hand, and a joystick configured for operation by a thumb of the one hand. The input device may include a plurality of motion sensors configured to determine position and orientation of the input device in space.

20 Claims, 31 Drawing Sheets

(51) Int. Cl.
*A61B 34/30* (2016.01)
*A61M 25/01* (2006.01)

(52) U.S. Cl.
CPC .... *A61B 1/00149* (2013.01); *A61B 2034/301* (2016.02); *A61B 2034/742* (2016.02); *A61M 25/0113* (2013.01)

(56) References Cited

U.S. PATENT DOCUMENTS

| | | | | |
|---|---|---|---|---|
| 5,876,325 | A * | 3/1999 | Mizuno | A61B 34/37 |
| | | | | 600/117 |
| 6,541,027 | B1 * | 4/2003 | Antoine | C12P 1/04 |
| | | | | 435/252.4 |
| 7,682,358 | B2 | 3/2010 | Gullickson et al. | |
| 7,686,816 | B2 | 3/2010 | Belef et al. | |
| 7,789,825 | B2 | 9/2010 | Nobis et al. | |
| 8,007,432 | B2 | 8/2011 | Vakharia et al. | |
| 8,808,168 | B2 | 8/2014 | Ettwein et al. | |
| 9,095,686 | B2 | 8/2015 | Zanne et al. | |
| 9,375,550 | B2 | 6/2016 | Tegg | |
| 9,402,604 | B2 | 8/2016 | Williams et al. | |
| 9,433,340 | B2 | 9/2016 | Jones et al. | |
| 10,667,673 | B2 | 6/2020 | Su et al. | |
| 10,881,832 | B2 | 1/2021 | Chu | |
| 2001/0004676 | A1 | 6/2001 | Ouchi | |
| 2004/0267093 | A1 | 12/2004 | Miyagi et al. | |
| 2005/0267327 | A1 | 12/2005 | Iizuka et al. | |
| 2007/0225754 | A1 | 9/2007 | Measamer et al. | |
| 2010/0191224 | A1 | 7/2010 | Butcher | |
| 2010/0210908 | A1 | 8/2010 | Ashida et al. | |
| 2012/0065470 | A1 * | 3/2012 | Olds | A61B 34/30 |
| | | | | 901/41 |
| 2012/0071752 | A1 | 3/2012 | Sewell et al. | |
| 2014/0275763 | A1 | 9/2014 | King et al. | |
| 2014/0316203 | A1 | 10/2014 | Carroux et al. | |
| 2015/0335862 | A1 | 11/2015 | Selkee | |
| 2016/0270825 | A1 | 9/2016 | Wentz et al. | |
| 2016/0324399 | A1 | 11/2016 | Banju et al. | |
| 2017/0143195 | A1 | 5/2017 | Yee et al. | |
| 2017/0215901 | A1 | 8/2017 | Harrah et al. | |
| 2019/0021707 | A1 | 1/2019 | Belsky et al. | |
| 2019/0029498 | A1 | 1/2019 | Mankowski et al. | |
| 2019/0192822 | A1 | 6/2019 | Kim et al. | |
| 2019/0208994 | A1 | 7/2019 | Davis | |
| 2019/0209810 | A1 | 7/2019 | Reid et al. | |
| 2019/0232027 | A1 | 8/2019 | Chu | |
| 2019/0313881 | A1 | 10/2019 | Francher | |
| 2019/0380562 | A1 | 12/2019 | Deuel et al. | |
| 2020/0046978 | A1 | 2/2020 | Kaufmann et al. | |
| 2020/0100647 | A1 | 4/2020 | Craig et al. | |
| 2020/0196834 | A1 | 6/2020 | Tah | |
| 2020/0222668 | A1 | 7/2020 | Wenderow et al. | |
| 2020/0345207 | A1 | 11/2020 | Nguyen et al. | |
| 2021/0015564 | A1 | 1/2021 | Vogele | |
| 2021/0045619 | A1 | 2/2021 | Sauer | |
| 2021/0045626 | A1 | 2/2021 | Hsu et al. | |
| 2021/0085153 | A1 | 3/2021 | Chu et al. | |
| 2021/0186304 | A1 | 6/2021 | Joshi et al. | |
| 2021/0186306 | A1 | 6/2021 | Komuro | |
| 2021/0251709 | A1 | 8/2021 | Sharon et al. | |
| 2021/0393338 | A1 | 12/2021 | Graetzel et al. | |
| 2022/0160207 | A1 | 5/2022 | Nycz et al. | |
| 2022/0280021 | A1 | 9/2022 | Chu | |
| 2022/0304548 | A1 | 9/2022 | Chu | |
| 2022/0362518 | A1 | 11/2022 | Gu et al. | |

FOREIGN PATENT DOCUMENTS

| | | | |
|---|---|---|---|
| DE | 202010009234 | U1 | 12/2011 |
| GB | 2555111 | A | 4/2018 |
| JP | H09492 | A | 1/1997 |
| WO | 2020049718 | A1 | 3/2020 |
| WO | 2020160522 | A1 | 8/2020 |

OTHER PUBLICATIONS

Cho et al; "Evaluation of Performance Parameters of the Disposable Flexible Ureterorenoscope (Lithovue) in Patients with Renal Stones: A Prospective, Observational, Single-Arm, Multicenter Study," Scientific Reports, vol. 8:9795, 6 pages, Published online: Jun. 28, 2018.

Tian et al; "Cannulation Time is a More Accurate Measure of Cannulation Difficulty in Endoscopic Retrograde Cholangiopancreatography than the Number of Attempts," Gastroenterology Report, 1, pp. 193-197, Aug. 2013.

Tringali et al; "Endoscopic Retrograde Cholangiopancreatography: Indications, Patient Preparation and Complications," UpToDate®, Wolters Kluwer® 33 pages, Accessed Sep. 1, 2020.

International Search Report and Written Opinion dated Feb. 28, 2022 for International Application No. PCT/US2021/060305.

International Search Report and Written Opinion dated Jun. 10, 2022 for International Application No. PCT/US2022/018561.

Boston Scientific, Lithovue Empower™, Retrieval Deployment Device, Brochure, URO-554-002-AA, 4 pages, Jul. 2018.

International Search Report and Written Opinion dated Jun. 1, 2022 for International Application No. PCT/US2022/020951.

International Search Report and Written Opinion dated Aug. 8, 2022 for International Application No. PCT/US2022/028757.

Invitation to Pay Additional Fees and, Where Applicable, Protest Fee for International Application No. PCT/US2023/023371, mailing date Sep. 14, 2023.

International Search Report and Written Opinion dated Sep. 8, 2023 for International Application No. PCT/US2023/023355.

International Search Report and Written Opinion dated Sep. 15, 2023 for International Application No. PCT/US2023/023383.

* cited by examiner

50

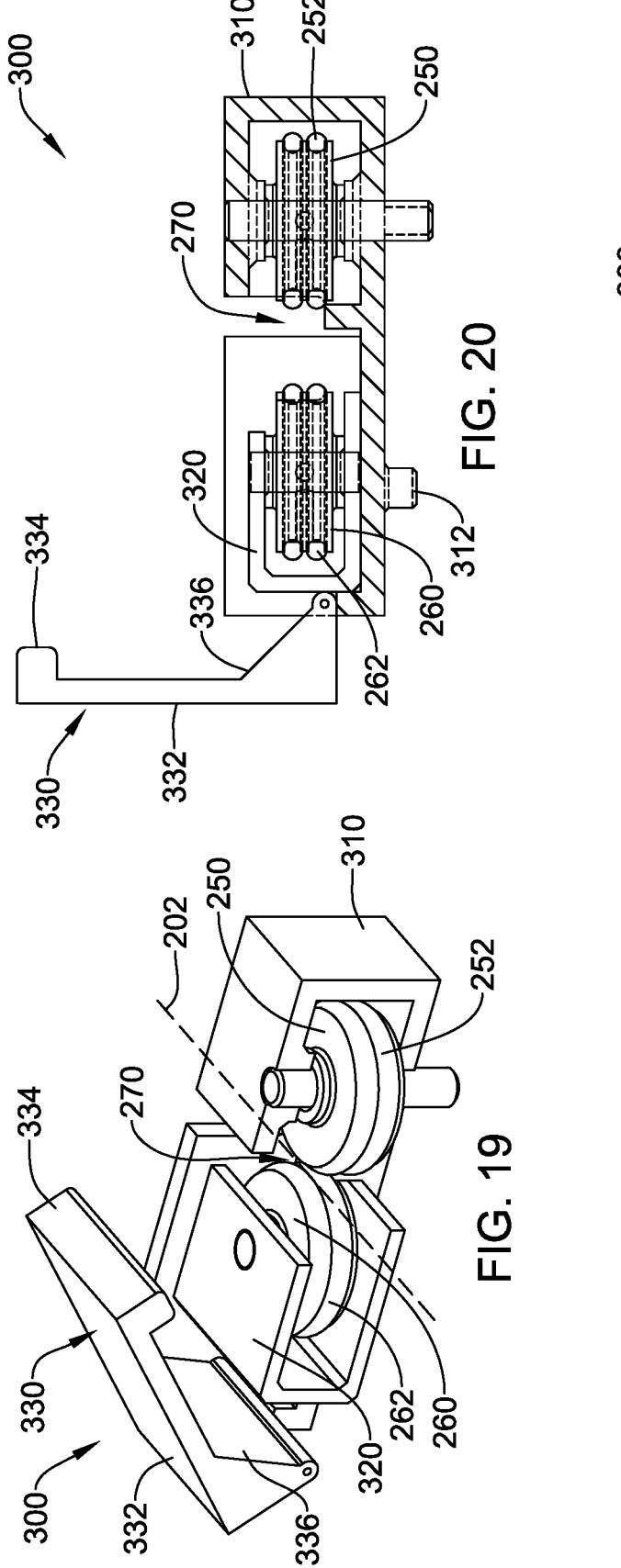
FIG. 19
FIG. 20
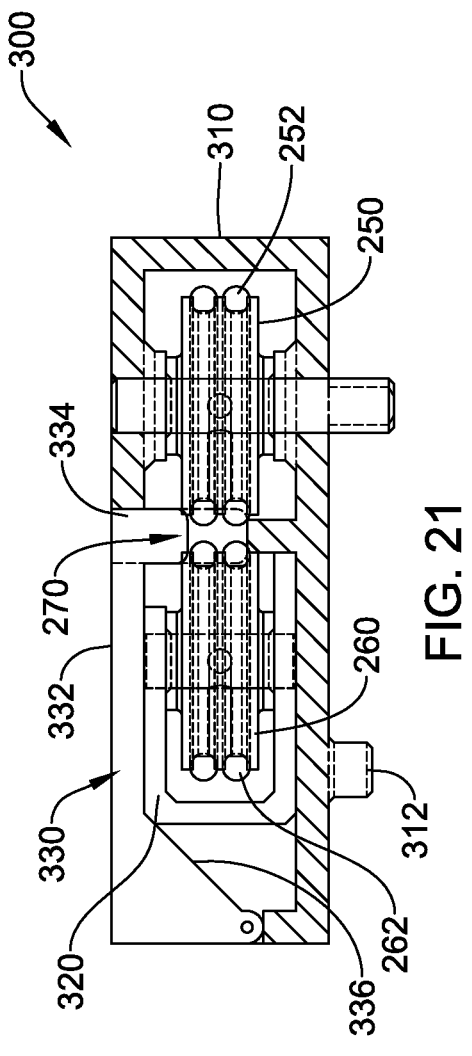
FIG. 21

ATTACHMENT MECHANISM FOR USING AN ENDOSCOPE WITH A SURGICAL ROBOT

CROSS-REFERENCE TO RELATED APPLICATIONS

This application claims the benefit of U.S. Provisional Patent Application Ser. No. 63/345,532, filed May 25, 2022, which is incorporated herein by reference.

TECHNICAL FIELD

The present disclosure pertains to medical devices and systems, and methods for manufacturing and using medical devices and systems. More particularly, the present disclosure pertains to endoscopic devices and surgical systems for using endoscopic devices with surgical robots.

BACKGROUND

Endoscopic devices are used for various diagnostic and surgical procedures. For example, flexible ureteroscopes are utilized in the examination and treatment of kidneys and may generally include features which improve treatment site accessibility and patient comfort. Flexible endoscopic devices may be provided with a flexible shaft and/or a flexible tip section that is controlled by a physician via manipulation of various components attached to the scope's handle. Such manipulation enables the physician to maneuver the tip of the scope to various locations within the body (e.g., various locations within the kidney). Additionally, endoscopes are typically used in conjunction with other medical devices during a medical procedure. For example, urologists may use a flexible ureteroscope in combination with both a laser fiber and a retrieval device (e.g., retrieval basket) to pulverize kidney stones and/or to remove debris from the body. Accordingly, these procedures may require not only manipulating various features of the endoscope to control the tip of the scope, but also to introduce and manipulate ancillary devices used in conjunction with the endoscope.

Additionally, the field of medical robotics has been growing rapidly with innovations focused on simplifying procedures, improving patient outcomes, and reducing costs. Surgical robots may provide stable and precise movements. In some fields, integrating robot controls into surgical procedures may decrease the learning curve and skill level needed to perform various procedures, thereby allowing more physicians to successfully treat patients. Surgical robots may enhance precision, flexibility, and control during the procedure, and may allow the surgeon improved visibility of the surgical site compared to traditional techniques via integrated and/or associated camera systems. In some cases, surgical robots may make minimally invasive surgeries possible, thereby reducing complications, patient pain, recovery time, and/or scarring.

During endoscopy and urology procedures, flexible endoscopes and accessory devices may be used to access the anatomy. Navigating the flexible endoscope into and/or through the anatomy may be challenging. Typically, the handle alone cannot be used to insert and/or advance the shaft because the shaft tends to buckle when encountering opposing forces such as an obstruction or when encountering tortuous anatomy. Commonly, a practitioner may use two hands to operate an endoscope—one hand to control shaft rotation and tip deflection via the handle and the other hand controlling and inserting the flexible shaft into the anatomy. Additionally, repeatability of various actions may be difficult and/or may be physically taxing to the user. Manual manipulation of the endoscope may introduce opportunities for unwanted hand movements to be transmitted to the patient's anatomy. Surgical robotics may offer opportunities for various improvements if they can be adapted for use with a manual endoscope.

The disclosure relates to devices and/or methods of using an endoscope with a surgical robot. Of the known medical devices, systems, and methods, each has certain advantages and disadvantages. There is an ongoing need to provide alternative medical devices and systems, as well as alternative methods for manufacturing and using medical devices and systems.

SUMMARY

In one example, a surgical system for use with a surgical robot may comprise an endoscope including a handle and an elongate shaft extending distally from the handle, an attachment mechanism including a fixture configured to receive the handle of the endoscope and a mounting structure configured to attach the fixture to the surgical robot, a motorized introducer apparatus spaced apart from the surgical robot and configured to translate the elongate shaft of the endoscope relative to a patient, and an input device configured to be operated using one hand only. The input device may include a plurality of tactile buttons operable using the one hand, and a joystick configured for operation by a thumb of the one hand.

In addition or alternatively to any example described herein, the plurality of tactile buttons includes a set home button and a go home button.

In addition or alternatively to any example described herein, the plurality of tactile buttons includes an extend button configured to advance the shaft of the endoscope through the motorized introducer apparatus, and a retract button configured to retract the shaft of the endoscope through the motorized introducer apparatus.

In addition or alternatively to any example described herein, the plurality of tactile buttons includes a lock mode button configured to lock the surgical robot and the attachment mechanism in their current configuration.

In addition or alternatively to any example described herein, the plurality of tactile buttons includes an operational mode button configured to permit all movement functionality of the surgical robot and the attachment mechanism.

In addition or alternatively to any example described herein, the fixture includes a first motor operably coupled to a first drive mechanism, the first drive mechanism being configured to engage the handle of the endoscope to operate a deflection mechanism of the endoscope. The mounting structure includes a second motor operably coupled to a second drive mechanism, the second drive mechanism being configured to rotate the fixture relative to the mounting structure.

In addition or alternatively to any example described herein, the joystick is configured to control the first motor and the second motor.

In addition or alternatively to any example described herein, the plurality of tactile buttons includes a manual positioning mode button configured to permit manual movement of the surgical robot without any other input from the input device.

In addition or alternatively to any example described herein, the input device includes at least one feedback element each operatively connected to a corresponding sensor disposed at a distal tip of the elongate shaft of the endoscope.

In addition or alternatively to any example described herein, a surgical system for use with a surgical robot may comprise an endoscope including a handle and an elongate shaft extending distally from the handle, an attachment mechanism including a fixture configured to receive the handle of the endoscope and a mounting structure configured to attach the fixture to the surgical robot, a motorized introducer apparatus spaced apart from the surgical robot and configured to translate the elongate shaft of the endoscope relative to a patient, and an input device configured to be operated using one hand only. The input device may include a plurality of tactile buttons operable using the one hand, the plurality of tactile buttons including a clutch button; a joystick configured for operation by a thumb of the one hand; and a plurality of motion sensors configured to determine position and orientation of the input device in space. Movement of the input device in space while the clutch button is depressed may control movement of at least some joints of the surgical robot. Movement of the surgical robot may be prevented when the clutch button is released.

In addition or alternatively to any example described herein, the plurality of tactile buttons includes a set home button and a go home button.

In addition or alternatively to any example described herein, the plurality of tactile buttons includes a calibration button.

In addition or alternatively to any example described herein, the plurality of tactile buttons includes a speed mode button.

In addition or alternatively to any example described herein, the plurality of tactile buttons includes at least one of the following: an irrigation button configured to activate fluid irrigation through the endoscope, an image capture button configured to capture an image seen via a camera disposed within the endoscope, and a memory button configured to save a second stored position of the surgical robot.

In addition or alternatively to any example described herein, the fixture includes a first motor operably coupled to a first drive mechanism, the first drive mechanism being configured to engage the handle of the endoscope to operate a deflection mechanism of the endoscope. The mounting structure includes a second motor operably coupled to a second drive mechanism, the second drive mechanism being configured to rotate the fixture relative to the mounting structure.

In addition or alternatively to any example described herein, the joystick is configured to control the second motor and the motorized introducer apparatus.

In addition or alternatively to any example described herein, the plurality of tactile buttons includes a deflection button configured to control the first motor.

In addition or alternatively to any example described herein, movement of the input device about a first axis while the clutch button is depressed causes movement of a first joint of the surgical robot about a first robot axis.

In addition or alternatively to any example described herein, movement of the input device about a second axis while the clutch button is depressed causes movement of a second joint of the surgical robot about a second robot axis.

In addition or alternatively to any example described herein, a surgical system for use with a surgical robot may comprise an endoscope including a handle and an elongate shaft extending distally from the handle, an attachment mechanism including a fixture configured to receive the handle of the endoscope and a mounting structure configured to attach the fixture to the surgical robot, a motorized introducer apparatus spaced apart from the surgical robot and configured to translate the elongate shaft of the endoscope relative to a patient, and an input device configured to control motion of the surgical robot and/or the motorized introducer apparatus using one hand only.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which:

FIGS. 19-21 illustrate selected aspects of a configuration of the motorized introducer apparatus of FIG. 18.

Figure 1:
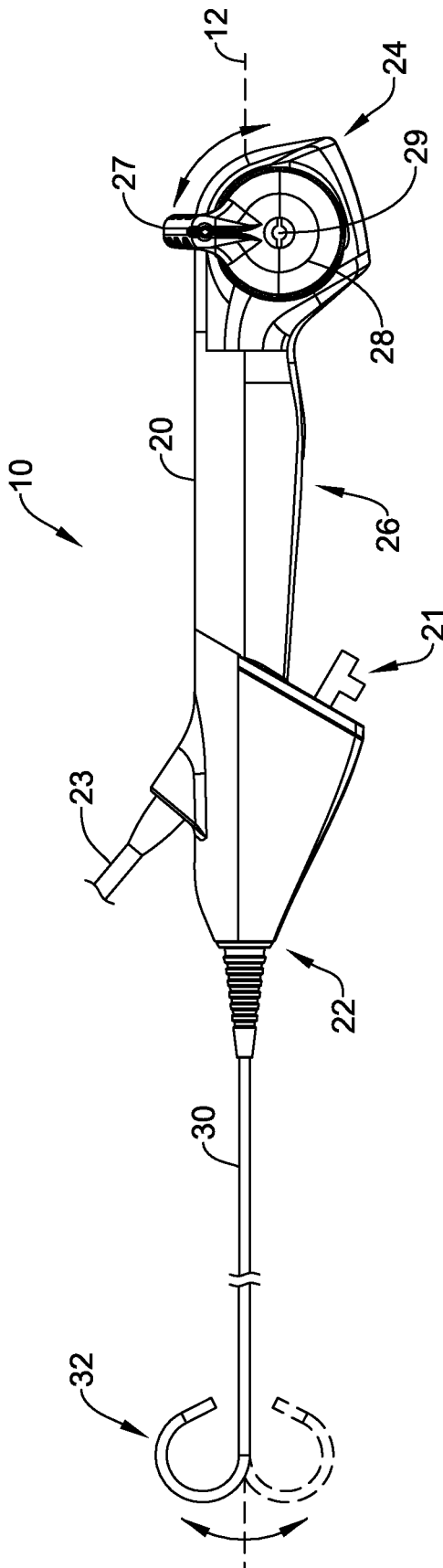
FIG. 1 is a schematic illustration of an endoscope.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate exemplary aspects of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, all elements of the disclosure are not necessarily shown in each figure or discussed in detail below. However, it will be understood that the following discussion may apply equally to any and/or all of the components for which there are more than one, unless explicitly stated to the contrary.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of medical devices and/or systems and methods of using the same. It should be noted that in any given figure, some features of the endoprosthesis or stent may not be shown, or may be shown schematically, for simplicity. Additional details regarding some of the components of the system may be illustrated in other figures in greater detail. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. As such, it will be understood that the following discussion may apply equally to any and/or all of the components for which there are more than one within the endoprosthesis or stent, unless explicitly stated to the contrary.

In any given figure, some features may not be shown, or may be shown schematically, for clarity and/or simplicity. Additional details regarding some components and/or method steps may be illustrated in other figures in greater detail. The devices and/or methods disclosed herein may provide a number of desirable features and benefits as described in more detail below.

FIG. 1 illustrates selected aspects of an endoscope 10. The endoscope 10 may be any one of a plurality of endoscopes. In some embodiments, the plurality of endoscopes may be known in the prior art. In at least some embodiments, the endoscope 10 may be a flexible ureteroscope. The endoscope 10 may including a handle 20 and an elongate shaft 30 extending distally from the handle 20. The endoscope 10 and/or the handle 20 may include a longitudinal axis 12 extending generally along the handle 20 and/or the elongate shaft 30. In some embodiments, the longitudinal axis 12 may be coaxial with the elongate shaft 30.

The elongate shaft 30 of the endoscope 10 may include a deflectable distal tip 32 and the elongate shaft 30 may have a length of about 26.5 inches (about 67.3 centimeters). In some embodiments, the elongate shaft 30 may have a length of about 15 inches (about 38.1 centimeters), about 20 inches (about 50.8 centimeters), about 25 inches (about 63.5 centimeters), about 28 inches (about 71.1 centimeters), about 30 inches (about 76.2 centimeters), about 35 inches (about 88.9 centimeters), etc.

The handle 20 of the endoscope 10 may include a distal end 22, a proximal end 24, and a medial region 26 positioned between the distal end 22 and the proximal end 24. The medial region 26 may be sized, shaped, and/or configured to be gripped by a hand of a user. In general, the elongate shaft 30 may take the form of a polymer or metal tube. In some embodiments, the elongate shaft 30 may be constructed with a reinforcing braid, liner, web, weave, etc. The elongate shaft 30 may include a lumen defining a working channel extending through the elongate shaft 30 from a distal end region of the elongate shaft 30 to an access port 21 at and/or connected to the handle 20. In some embodiments, the elongate shaft 30 may include multiple working channels, as desired.

The deflectable distal tip 32 of the elongate shaft 30 of the endoscope 10 may include optics and illumination means disposed therein. The optics and illumination means may be configured to provide optical visualization of the area of the patient being treated and/or traversed by the deflectable distal tip 32. The handle 20 of the endoscope 10 may include an electronics and/or optics connector 23 configured to connect the optics and illumination means of the endoscope 10 to a controller, a monitor, a display, a computer, etc.

The handle 20 may include a deflection mechanism 28 operatively connected to the deflectable distal tip 32 of the elongate shaft 30, which may be used to control movement of the deflectable distal tip 32 of the elongate shaft 30 during operation. For example, the deflection mechanism 28 may control up and down movement or deflection of the deflectable distal tip 32 of the elongate shaft 30. The deflection mechanism 28 may be disposed proximate the proximal end 24 of the handle 20. The deflection mechanism 28 may include a thumb lever 27 movable along an outer surface of the handle 20 and configured to be engaged by and/or actuated by a thumb of the hand gripping the medial region 26. The deflection mechanism 28 may include a keyed aperture 29 formed therein. The deflection mechanism 28 may include one or more gears, pulleys, cables, wires, filaments, etc. disposed within the handle 20 and/or extending into the elongate shaft 30. The deflection mechanism 28 may include a self-locking or friction lock type knob which maintains the deflection mechanism 28 and/or the deflectable distal tip 32 at its deflected position after being released.

The handle 20 may also include one or a plurality of buttons, which may be used to activate irrigation and/or aspiration of a fluid such as air, saline, water, and/or blood, etc. through a lumen of the endoscope 10 or perform other functions as desired. These are just examples. Other configurations, variations, and/or features for the endoscope 10 are also contemplated.

Figure 2:
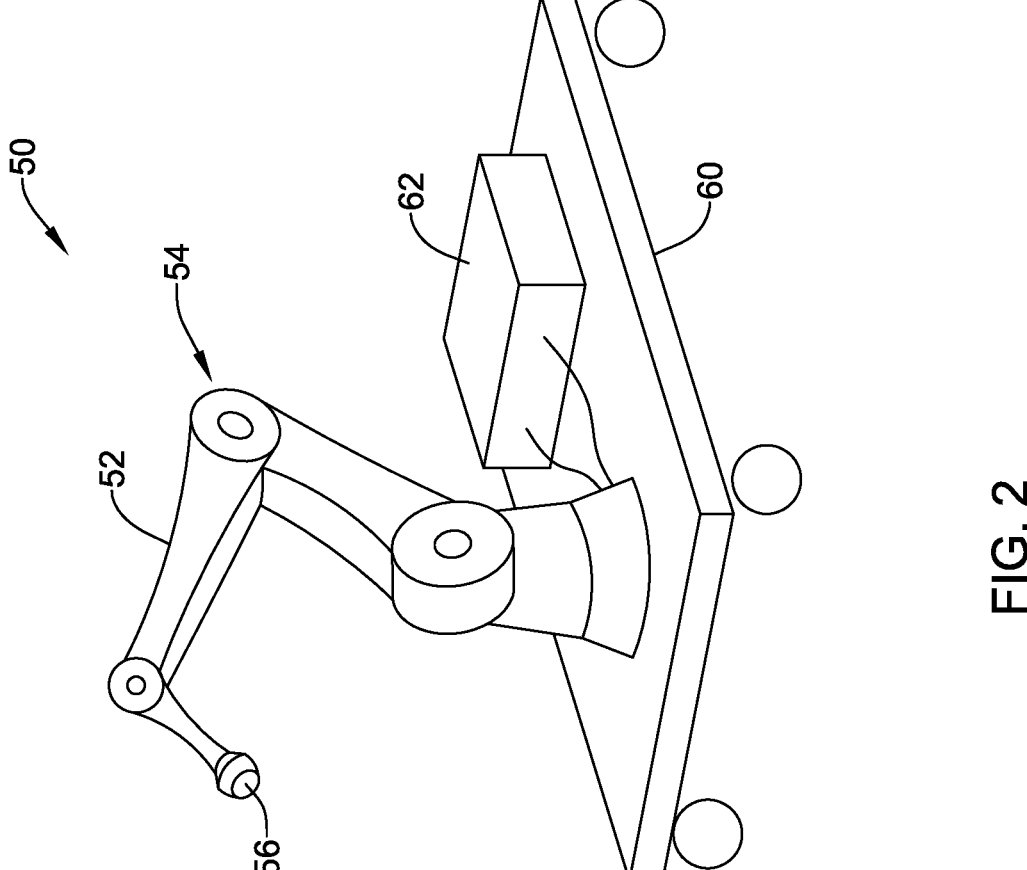
FIG. 2 is a schematic illustration of a surgical robot.
Figure 3:
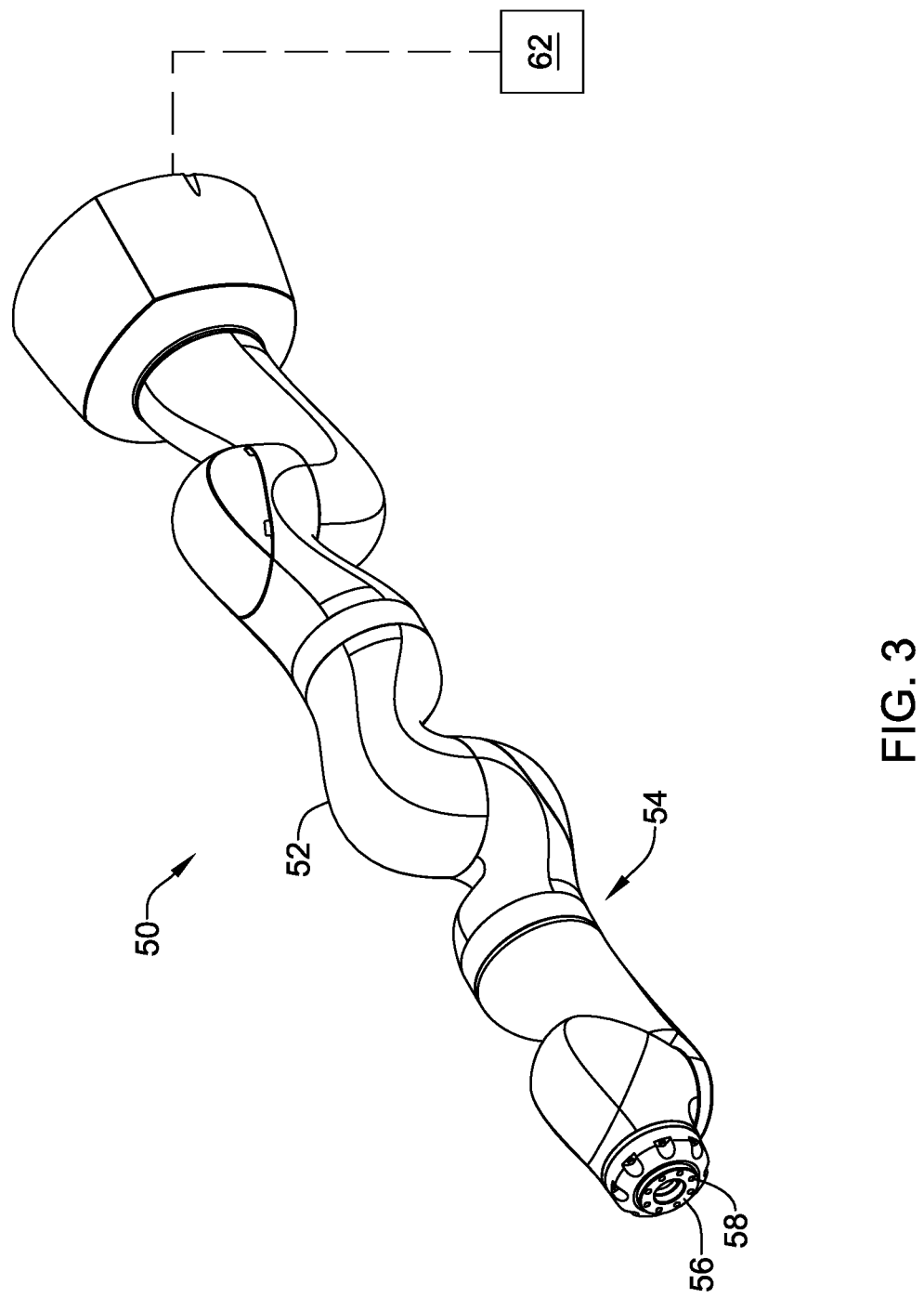
FIG. 3 is a schematic illustration of a surgical robot.

FIGS. 2 and 3 schematically illustrate examples of a surgical robot 50. In some embodiments, the surgical robot 50 may be mounted to a mobile platform 60. In some embodiments, the surgical robot 50 may be mounted to a fixed structure. In some embodiments, the surgical robot 50 may include an arm 52 having a plurality of joints 54. In some embodiments, the plurality of joints 54 may include one or more hinge joints, one or more rotating joints, and/or combinations thereof. Each joint may include and/or define an axis of movement. The surgical robot 50 may include a plurality of axes of movement.

The surgical robot 50 may include a distal flange 56 configured to receive, mount, and/or attach one or more devices, accessories, tools, etc. In some embodiments, the surgical robot 50 may include a controller 62 operatively coupled to the surgical robot 50. In some embodiments, the controller 62 may be operatively coupled to the surgical robot 50 via one or more wires or cables. In some embodiments, the controller 62 may be operatively coupled to the surgical robot 50 wirelessly. Combinations of these are also contemplated. The surgical robot 50 may include a plurality of sensors disposed within and/or on the surgical robot 50 and/or the arm 52. The plurality of sensors may be configured to detect relative positioning of the various parts and components of the surgical robot 50 and/or the arm 52.

In some embodiments, and as shown illustratively in FIG. 3, the surgical robot 50 may be a KUKA LBR Med robot from KUKA Deutschland GmbH. Other surgical robots are also contemplated for use with aspects of the present disclosure. Commercially available surgical robots may include emergency stopping and/or safety features built in. Some surgical robots may include a back-up power source in case of a power failure during the procedure. At least some surgical robots utilize a computer and/or a touchscreen input pad to control the surgical robot. At least some commercially available surgical robots require the input of specific positional data such as reference coordinates (e.g., X, Y, and Z) in order to move the surgical robot and/or translate the position of the arm, etc. and/or may not be conducive to dynamic movements.

Figure 4:
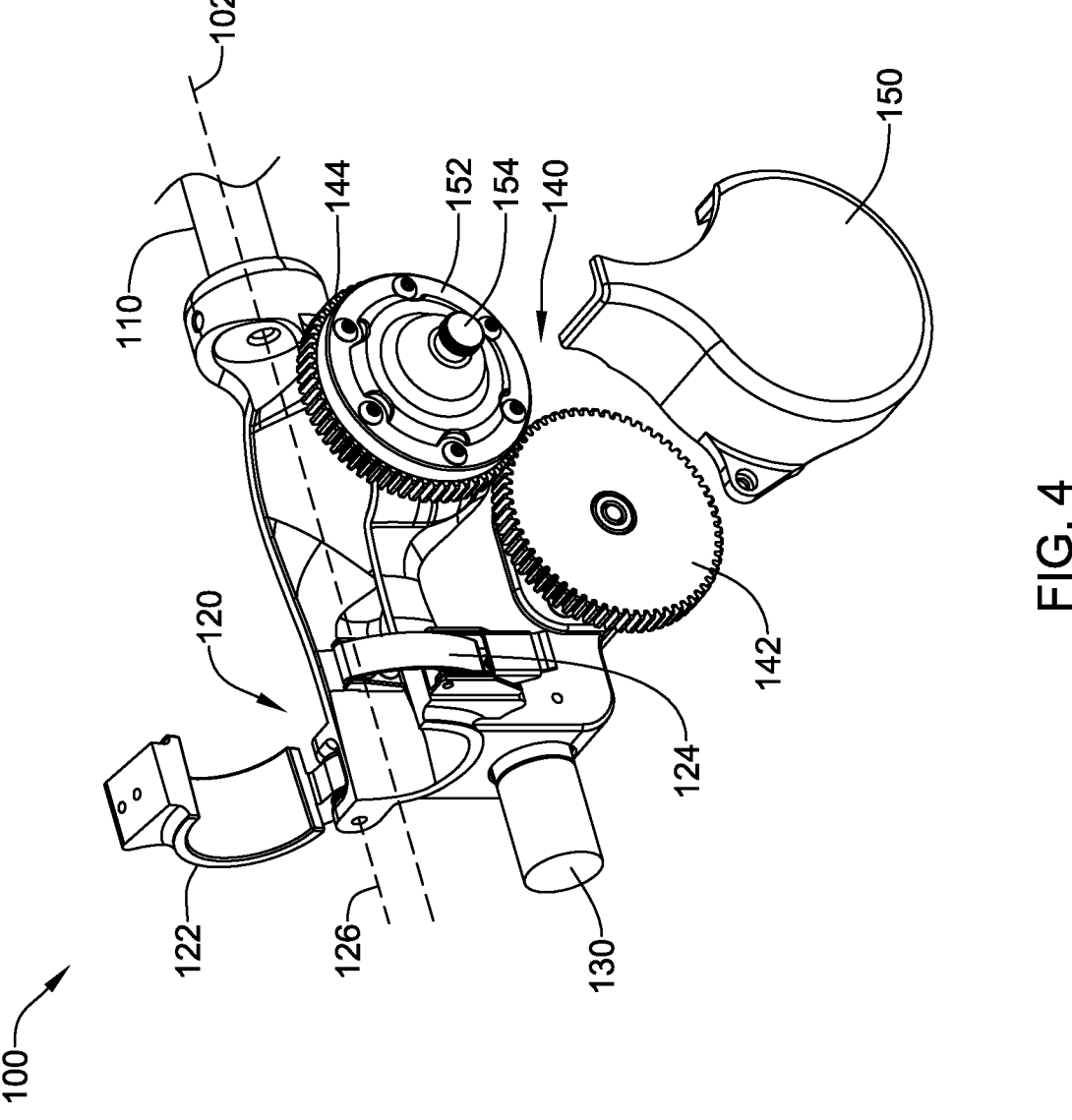
FIGS. 4-5 are partially exploded views of a fixture configured to receive a handle of an endoscope.
Figure 5:
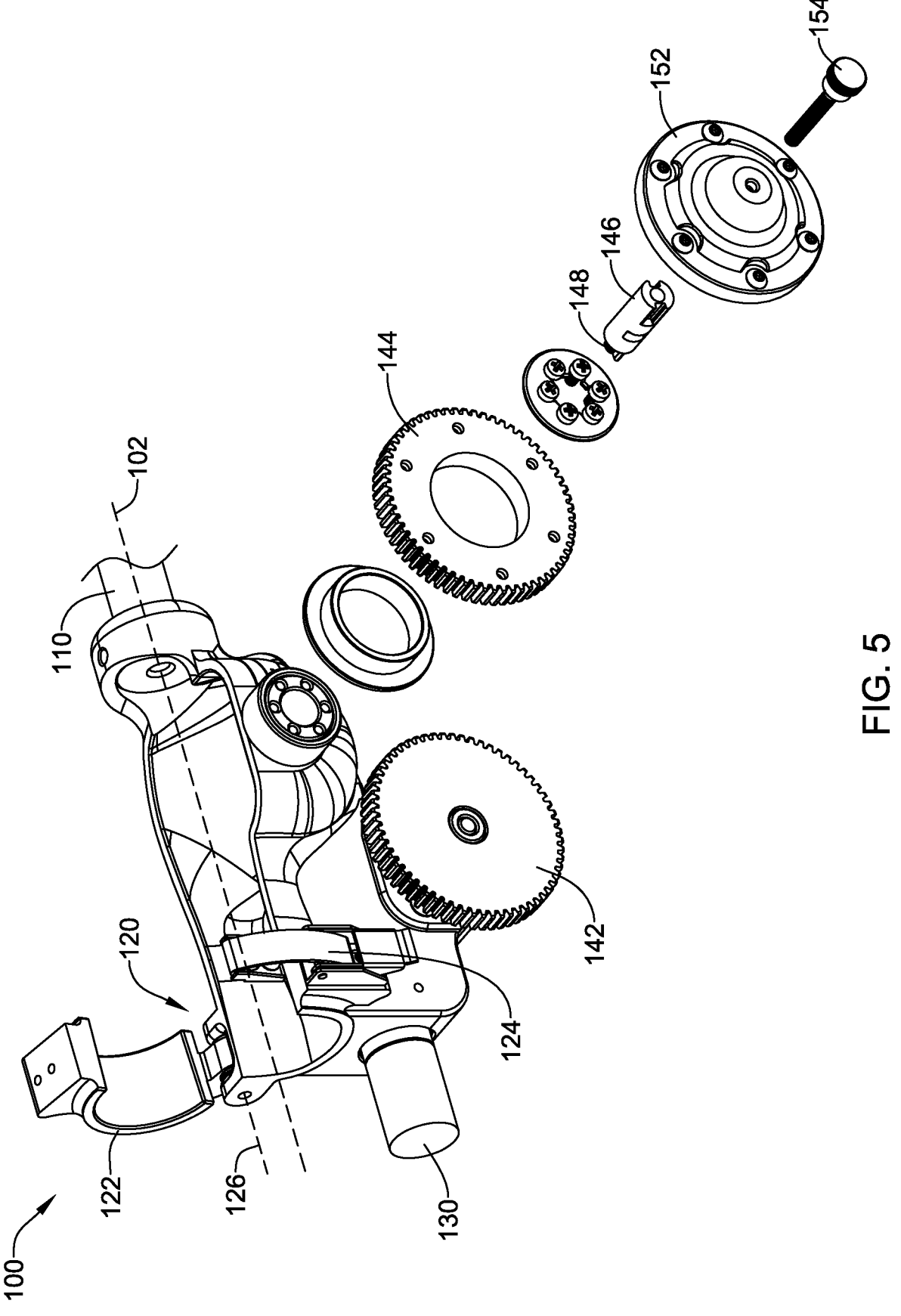
Figure 6:
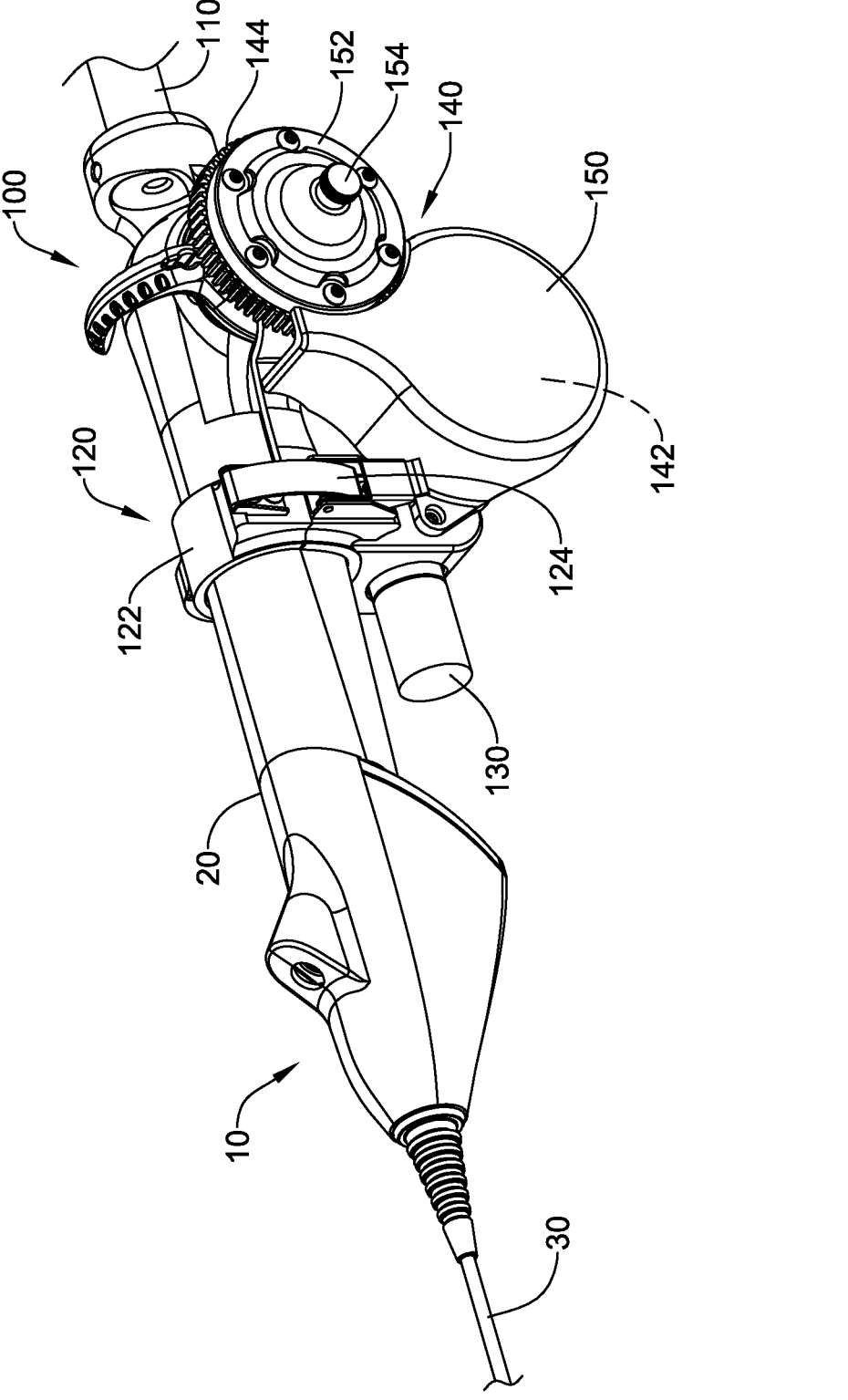
FIG. 6 illustrates the handle of an endoscope disposed within the fixture of FIGS. 4-5.

In some embodiments of the present disclosure, an attachment mechanism 90 (e.g., FIGS. 7-13) for using an endoscope 10 with a surgical robot 50 may include a fixture 100, as seen in FIGS. 4-5, configured to receive the handle 20 of the endoscope 10 such that the longitudinal axis 12 of the endoscope 10 and/or the handle 20 is oriented generally parallel with a longitudinal axis 102 of the fixture 100 and the elongate shaft 30 of the endoscope extends distally away from the fixture 100, as seen in FIG. 6. In some embodiments, the fixture 100 may include a shaft 110 fixedly secured to the fixture 100 and extending proximally from the fixture 100. In some embodiments, the shaft 110 may extend parallel to the longitudinal axis 102 of the fixture 100. In some embodiments, the shaft 110 may extend coaxial with the longitudinal axis 102 of the fixture 100.

In some embodiments, the fixture 100 may include a retaining mechanism 120 configured to releasably secure the handle 20 of the endoscope 10 to and/or within the fixture 100. In some embodiments, the retaining mechanism 120 may include a clamping portion 122 and a latching portion 124. In some embodiments, the clamping portion 122 may be movably attached to the fixture 100 and configured to rotate about a pivot axis 126 oriented generally parallel to the longitudinal axis of the fixture 100 between a closed configuration and an open configuration. The clamping portion 122 is shown in FIGS. 4 and 5 in the open configuration. In at least some embodiments, the clamping portion 122 may be configured to cooperate with the fixture 100 to surround at least a portion of the handle 20 of the endoscope 10 in the closed configuration, as seen in FIG. 6. The latching portion 124 may be configured to secure the clamping portion 122 relative to the fixture 100 in the closed configuration.

In some embodiments, the latching portion 124 may include one or more linkages configured to pivot away from the clamping portion 122 to release the clamping portion 122 and permit the clamping portion 122 to shift from the closed configuration to the open configuration. In some embodiments, the latching portion 124 may include a flexible strip configured to deflect around the clamping portion 122 as the retaining mechanism 120 is moved from the open configuration to the closed configuration and/or to release the clamping portion and permit the clamping portion 122 to shift from the closed configuration to the open configuration. In some embodiments, the latching portion 124 may snap to the clamping portion 122 in the closed configuration. Other configurations are also contemplated.

In some embodiments, the fixture 100 may include a first motor 130 operably coupled to a first drive mechanism 140. In some embodiments, the first motor 130 may be fixedly attached to the fixture 100. In some embodiments, the first drive mechanism 140 may be configured to engage the handle 20 of the endoscope 10 and/or the keyed aperture 29 to operate the deflection mechanism 28 of the endoscope 10. The first drive mechanism 140 may include a plurality of gears operably connecting the first motor 130 to a drive shaft 146 configured to engage the deflection mechanism 28. In some embodiments, the plurality of gears may include a first gear 142 and a second gear 144, as discussed herein.

In some embodiments, the plurality of gears may include a worm and/or a shaft (not shown) coupled to the first motor 130 and configured to rotate the first gear 142. In at least some embodiments, the second gear 144 may be directly engaged with the first gear 142. In some embodiments, the fixture 100 and/or the first drive mechanism 140 may include a first drive mechanism cover 150 attachable to the fixture 100 over at least the first gear 142. While not explicitly necessary for the first drive mechanism 140 to function properly, the first drive mechanism cover 150 may be provided to eliminate one or more pinch points and/or to reduce contamination and/or interference with the first drive mechanism 140.

As seen in the partially exploded view of FIG. 5, the second gear 144 may be operatively coupled to the drive shaft 146. The drive shaft 146 may include a keyed tip 148 configured to engage the keyed aperture 29 and/or the deflection mechanism 28. In some embodiments, the fixture 100 and/or the first drive mechanism 140 may include a second gear cover 152 removably attached to the second gear 144. The second gear cover 152 may be nonrotatable relative to the second gear 144. The second gear cover 152 may include a keyed structure configured to nonrotatably engage a first end of the drive shaft 146 opposite the keyed tip 148. The drive shaft 146 may be secured to the second gear cover 152 by a fastener 154, such as a bolt, a screw, etc. Some suitable but non-limiting materials for the fixture 100, the shaft 110, the retaining mechanism 120, the first drive mechanism 140, the first drive mechanism cover 150, and/or components or elements thereof, for example metallic materials, polymeric materials, combinations thereof, etc. are described below.

Figure 7:
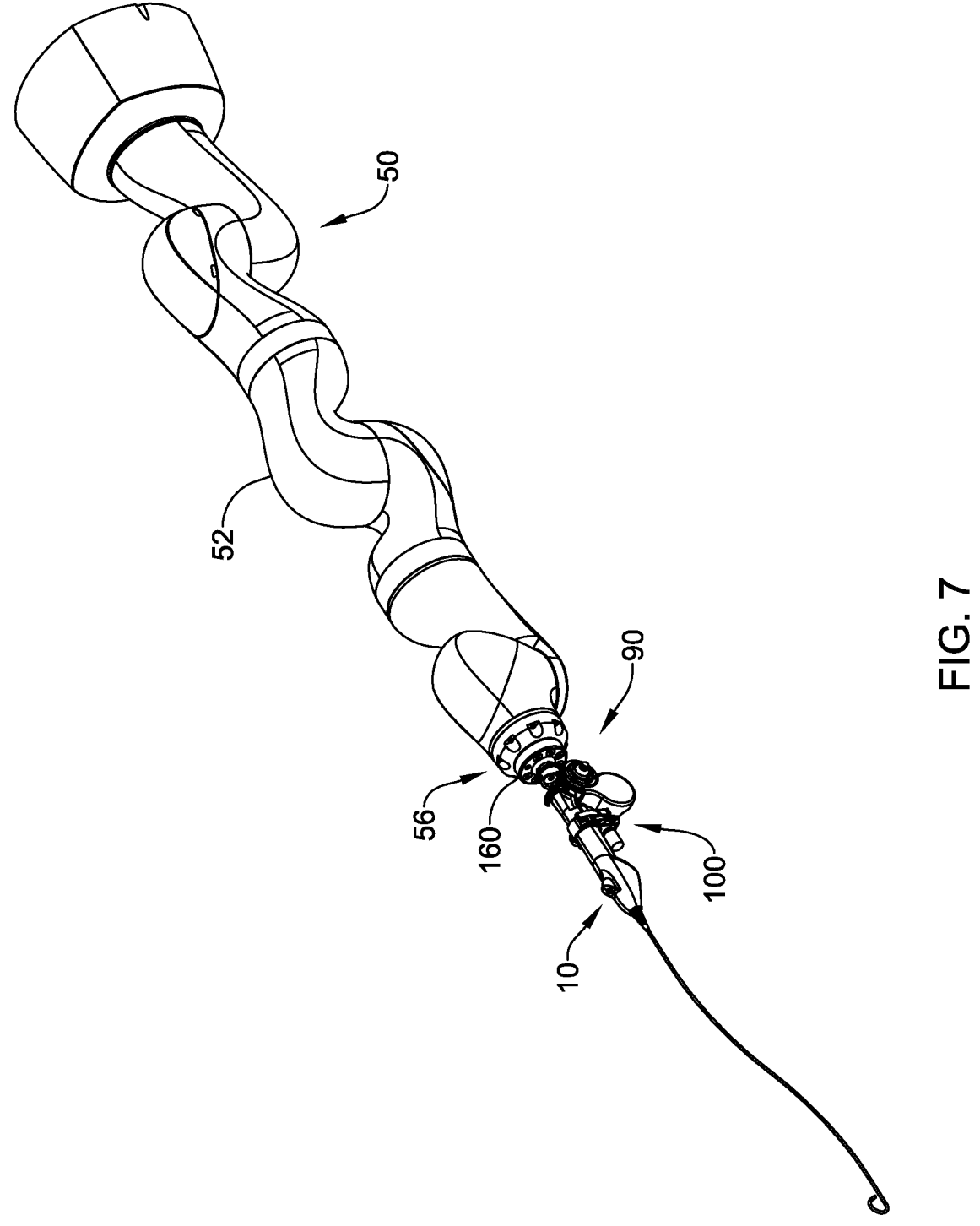
FIG. 7 is a schematic illustration of the endoscope and fixture of FIG. 6 attached to the surgical robot of FIG. 3.

As seen schematically in FIG. 7, the attachment mechanism 90 may be configured to couple the endoscope 10 with the surgical robot 50 and/or the arm 52 of the surgical robot 50. In some embodiments, the attachment mechanism 90 may include a mounting structure 160 secured to the fixture 100. The mounting structure 160 may include be configured to attach the fixture 100 to the distal flange 56 of the surgical robot 50 and/or the arm 52 of the surgical robot 50.

Figure 8:
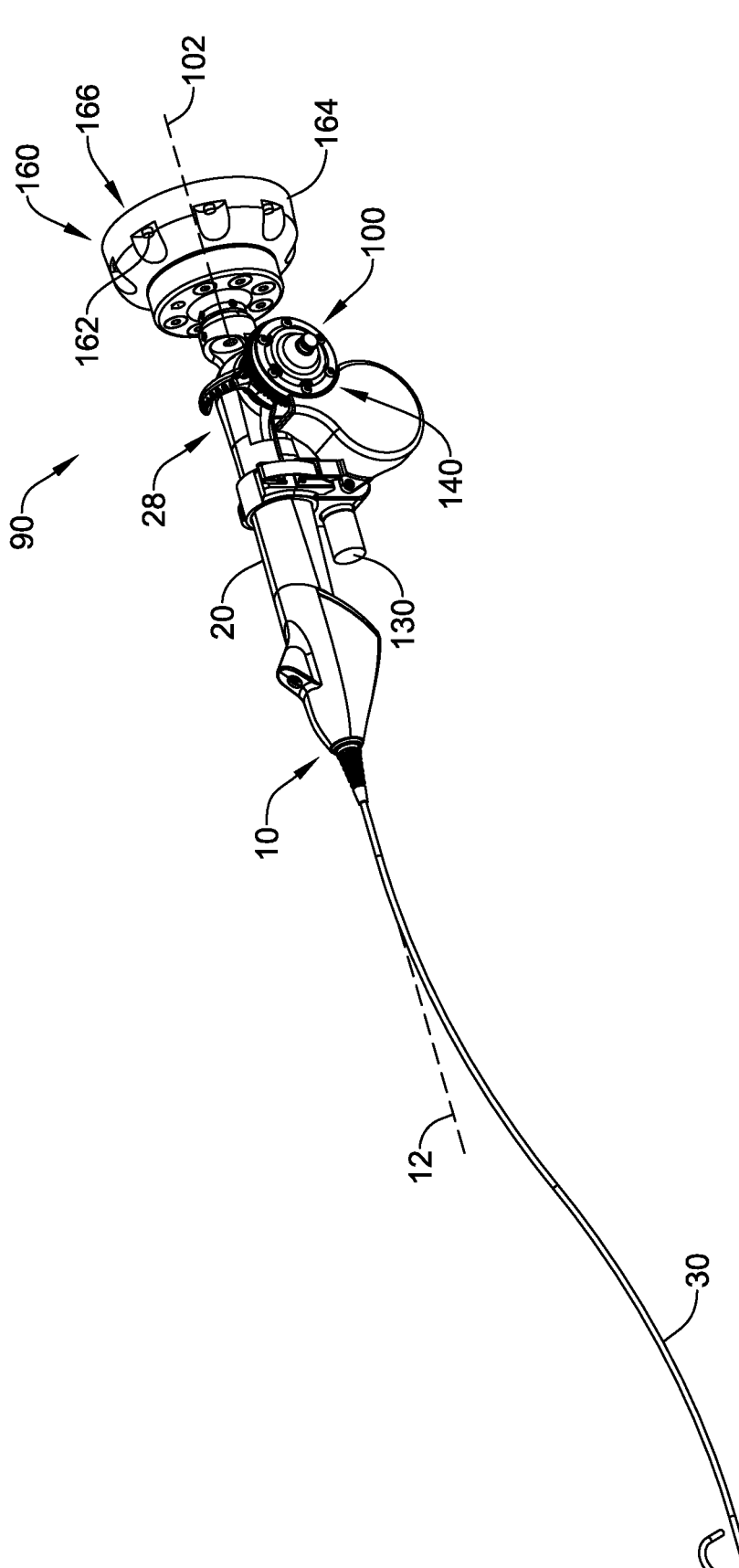
FIG. 8 illustrates selected aspects of an attachment mechanism for using an endoscope with a surgical robot.
Figure 9:
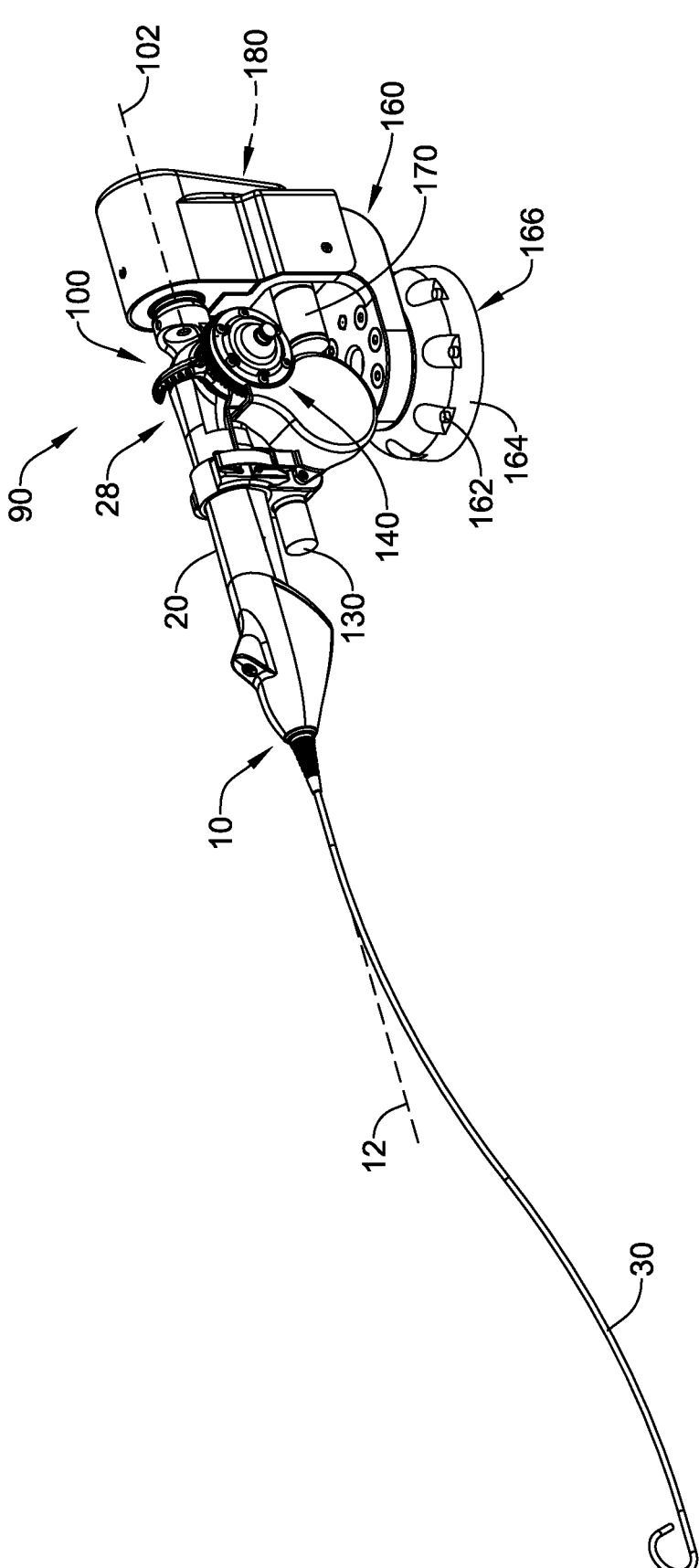
FIG. 9 illustrates selected aspects of an attachment mechanism for using an endoscope with a surgical robot.
Figure 10:
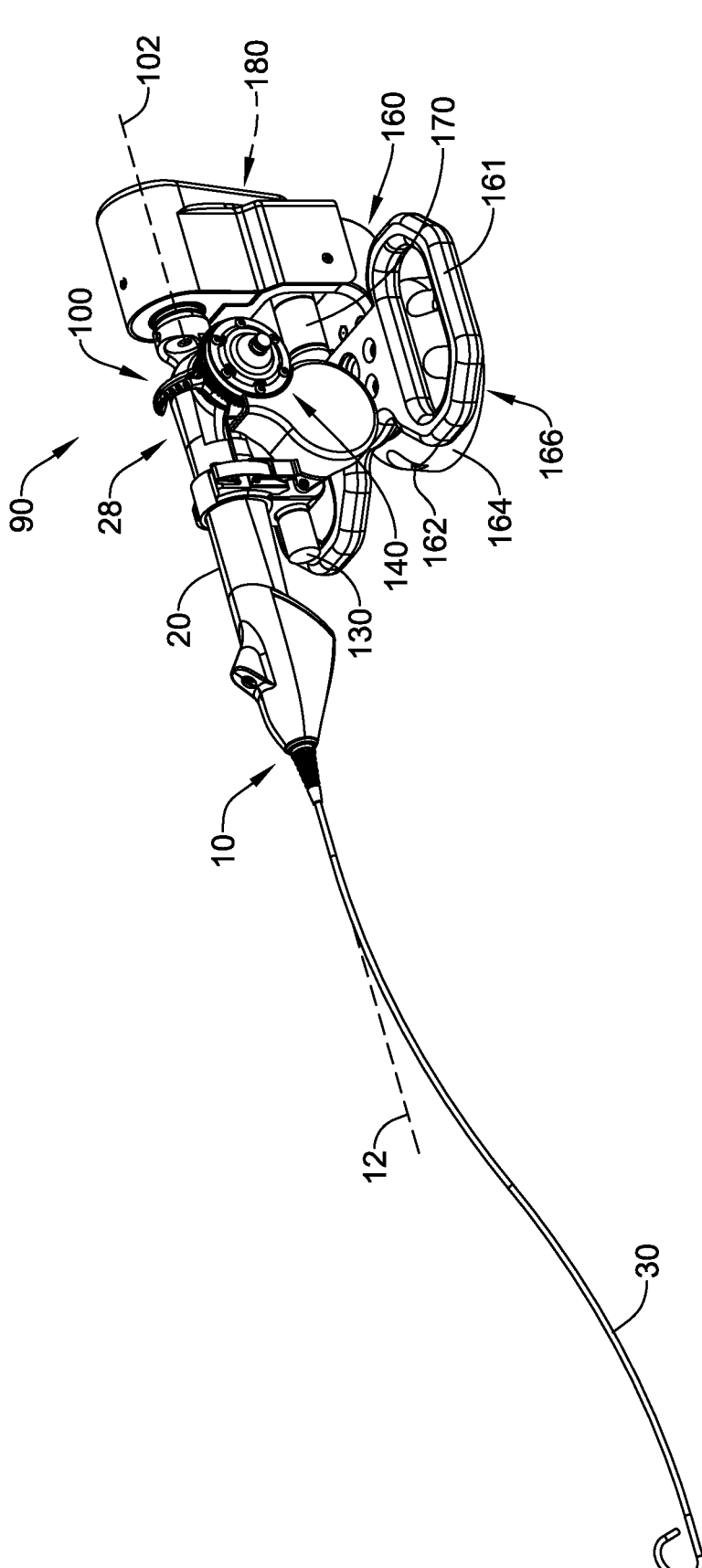
FIG. 10 illustrates selected aspects of an attachment mechanism for using an endoscope with a surgical robot.

FIGS. 8-10 illustrate some example configurations of an attachment mechanism 90 according to the disclosure. Other configurations are also contemplated. In some embodiments, the mounting structure 160 may include a plurality of apertures 162 formed in a mounting plate 164. The plurality of apertures 162 may be configured to align with a plurality of mounting holes 58 (e.g., FIG. 3) formed in the distal flange 56 of the surgical robot 50 and/or the arm 52 of the surgical robot 50. In at least some embodiments, the mounting plate 164 may include a substantially planar surface 166 configured to matingly engage with and/or abut the distal flange 56 of the surgical robot 50 and/or the arm 52 of the surgical robot 50. In some embodiments, the shaft 110 (not shown) may extend into and/or through the mounting structure 160.

In some embodiments, the longitudinal axis 102 of the fixture 100 may extend generally perpendicular to the mounting plate 164 and/or the substantially planar surface 166 of the mounting plate 164, as seen in FIG. 8. In this configuration, the handle 20 and the elongate shaft 30 of the endoscope 10 may be oriented generally perpendicular to the mounting plate 164 and/or the substantially planar surface 166 of the mounting plate 164. The handle 20 and the elongate shaft 30 may be oriented generally along and/or parallel to an entry path into the patient. The surgical robot 50, the arm 52 of the surgical robot 50, and/or the plurality of joints 54 of the surgical robot 50, individually or in combination, may be configured to rotate the fixture 100 and/or the endoscope 10, the handle 20, and/or the elongate shaft 30 about the longitudinal axis 102 of the fixture 100 and/or the longitudinal axis 12 of the endoscope 10 and/or the handle 20. The first motor 130 and/or the first drive mechanism 140 may be configured to operate the deflection mechanism 28, as described herein.

In some embodiments, the longitudinal axis 102 of the fixture 100 may extend generally parallel to the mounting plate 164 and/or the substantially planar surface 166 of the mounting plate 164, as seen in FIGS. 9 and 10. In this configuration, the handle 20 and the elongate shaft 30 of the endoscope 10 may be oriented generally parallel to the mounting plate 164 and/or the substantially planar surface 166 of the mounting plate 164. Similar to the configuration of FIG. 8, the first motor 130 and/or the first drive mechanism 140 may be configured to operate the deflection mechanism 28, as described herein.

In some embodiments, the mounting structure 160 may include a second motor 170 operably coupled to a second drive mechanism 180. In some embodiments, the second motor 170 may be fixedly attached to the mounting structure 160. The second drive mechanism 180 may be configured to rotate the fixture 100 relative to the mounting structure 160. In some embodiments, the second drive mechanism 180 may be configured to rotate the fixture 100 and/or the endoscope 10, the handle 20, and/or the elongate shaft 30 about the longitudinal axis 102 of the fixture 100. In some embodiments, the second drive mechanism 180 may be configured to rotate the fixture 100 relative to the mounting structure 160 to rotate the endoscope 10 and/or the handle 20 about the longitudinal axis 12 of the endoscope 10 and/or the handle 20. In some embodiments, the second drive mechanism 180 may be configured to rotate the fixture 100 and/or the handle 20 to rotate the elongate shaft 30. Compared to the configuration of FIG. 8, the addition of the second drive mechanism 180 in the configurations of FIGS. 9 and 10 may offer more direct control over rotation of the fixture 100 and/or the endoscope 10 while minimizing movement(s) of the surgical robot 50 and/or the arm 52 of the surgical robot 50. For example, the fixture 100 and/or the endoscope 10, the handle 20, and/or the elongate shaft 30 may be rotated without any movement of the surgical robot 50 and/or the arm 52 of the surgical robot 50.

In some embodiments, the mounting structure 160 may include at least one grab handle 161 fixedly attached to and/or integrally formed with the mounting plate 164, as seen in FIG. 10. The at least one grab handle 161 may be configured to permit manual positioning of the surgical robot 50 and/or the arm 52 of the surgical robot 50 when desired.

Figure 11:
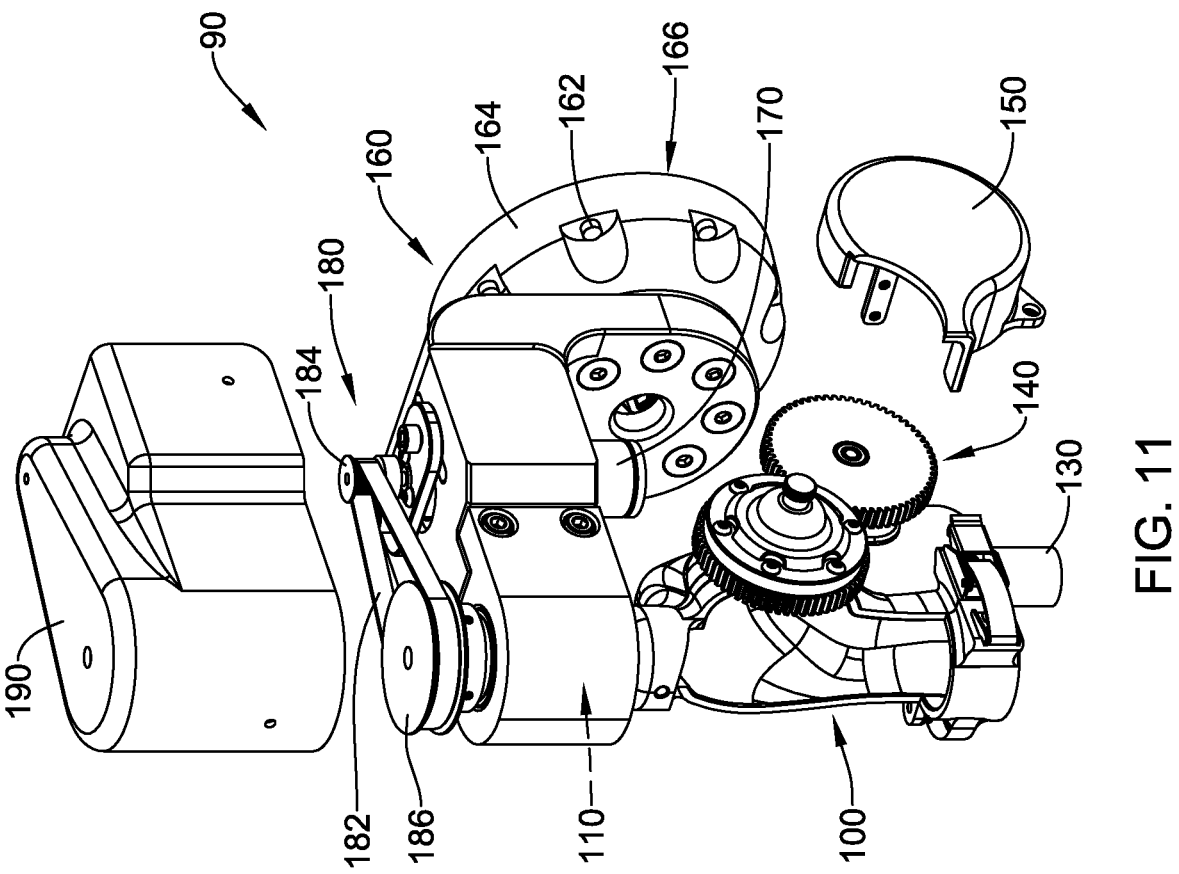
FIG. 11 is a partially exploded view illustrated selected aspects of the attachment mechanism of FIGS. 9-10.

In some embodiments, the second drive mechanism 180 may include a drive belt 182 engaged with a plurality of pulleys, as seen in FIG. 11. In some embodiments, the plurality of pulleys may include at least a first pulley 184 and a second pulley 186. Each of the plurality of pulleys may include an axis of rotation oriented generally parallel to the longitudinal axis 102 of the fixture 100. In some embodiments, the second drive mechanism 180 may include one or more gears, shafts, and/or coupling elements operably connecting the second motor 170 to the plurality of pulleys. In some embodiments, the one or more gears, shafts, and/or coupling elements operably connecting the second motor 170 to the plurality of pulleys may be disposed at least partially within and/or may extend at least partially through the mounting structure 160.

In some embodiments, the one or more gears, shafts, and/or coupling elements may include a worm and/or a shaft (not shown) coupled to the second motor 170 and configured to rotate the first pulley 184. In at least some embodiments, the second pulley 186 may be operably coupled to the first pulley 184 by the drive belt 182. In some embodiments, the second pulley 186 may be operably coupled to the shaft 110. In some embodiments, the mounting structure 160 and/or the second drive mechanism 180 may include a second drive mechanism cover 190 attachable to the mounting structure 160 over the plurality of pulleys. While not explicitly necessary for the second drive mechanism 180 to function properly, the second drive mechanism cover 190 may be provided to eliminate one or more pinch points and/or to reduce contamination and/or interference with the second drive mechanism 180.

Figure 12:
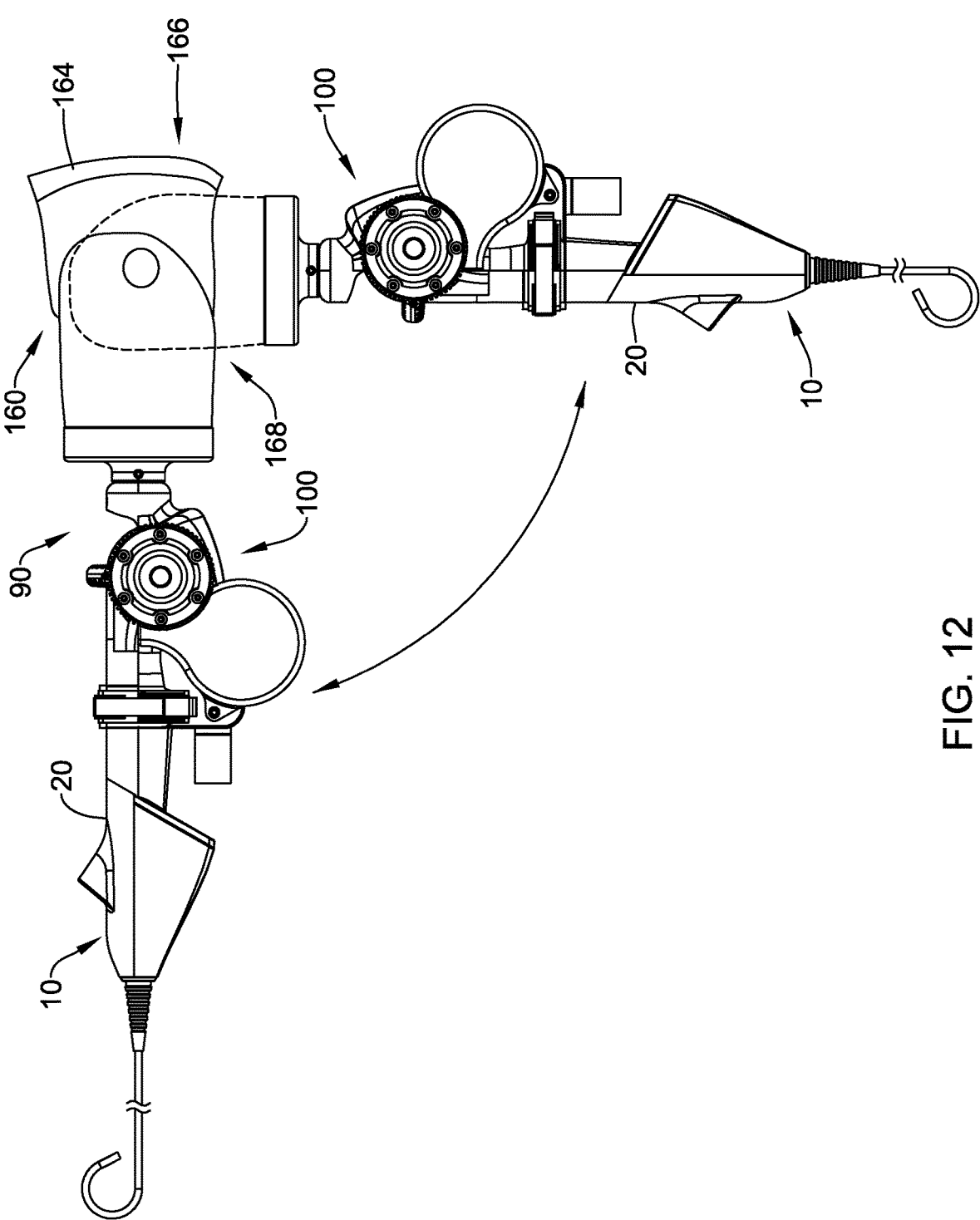
FIG. 12 is a schematic illustration of selected aspects of an alternative configuration of an attachment mechanism for using an endoscope with a surgical robot.

FIG. 12 is a schematic illustration showing selected aspects of an alternative configuration of an attachment mechanism 90 for using an endoscope 10 with a surgical robot 50. As above, the attachment mechanism 90 may include the fixture 100 and the mounting structure 160. In at least some embodiments, the mounting structure 160 may include a pivoting mechanism 168 disposed between the mounting plate 164 and the fixture 100. In some embodiments, the pivoting mechanism 168 may be configured to selectively position the fixture 100 and/or the handle 20 of the endoscope 10 disposable therein relative to the mounting plate 164, the surgical robot 50, and/or the arm 52 of the surgical robot 50 in one of two or more orientations.

In some embodiments, the pivoting mechanism 168 may be configured to shift the fixture 100 back and forth between a first position relative to the mounting plate 164, the surgical robot 50, and/or the arm 52 of the surgical robot 50 and a second position relative to the mounting plate 164, the surgical robot 50, and/or the arm 52 of the surgical robot 50. In some embodiments, the longitudinal axis 102 of the fixture 100 may extend generally perpendicular to the mounting plate 164 and/or the substantially planar surface 166 of the mounting plate 164 in the first position. In some embodiments, the longitudinal axis 102 of the fixture 100 may extend generally parallel to the mounting plate 164 and/or the substantially planar surface 166 of the mounting plate 164 in the second position. In some embodiments, the second position may be similar to a vertical orientation of the handle 20 used by a physician when manually operating the endoscope 10 in situ, which may facilitate transfer of the endoscope 10 into the fixture 100 without unintended movements of the endoscope 10 and/or the elongate shaft 30 in situ.

In at least some embodiments, the pivoting mechanism 168 may be manually actuated to shift the fixture 100 between the first position and the second position. For example, the pivoting mechanism 168 may be in a normally locked configuration in the first position and/or the second position such that the pivoting mechanism 168 is unable to pivot. The pivoting mechanism 168 may include a release button that is manually depressed by the operator to release the pivoting mechanism 168 from the normally locked configuration to an unlocked configuration. In the unlocked configuration, the pivoting mechanism 168 may be free to pivot the fixture 100 between the first position and the second position. In some embodiments, the normally locked configuration and/or the release button may be automatically reengaged when the pivoting mechanism 168 arrives at or achieves the first position and/or the second position. In one nonlimiting example, the release button may be spring loaded. In some alternative embodiments, the pivoting mechanism 168 and/or the release button may be automated and/or may be actuated electrically, such as with a motor or an actuator. Other configurations, including combinations thereof, are also contemplated.

In at least some embodiments, when the fixture 100 is positioned in the first position, the surgical robot 50, the arm 52 of the surgical robot 50, and/or a distalmost joint of the plurality of joints 54 of the surgical robot 50 may be configured to rotate the mounting plate 164, thereby rotating the fixture 100 and the mounting structure 160 about the longitudinal axis 102, thereby rotating the endoscope 10, the handle 20, and/or the elongate shaft 30. In some embodiments, when the fixture 100 is positioned in the second position, the surgical robot 50, the arm 52 of the surgical robot 50, and/or the distalmost joint of the plurality of joints 54 of the surgical robot 50 may be configured to rotate the mounting plate 164, thereby rotating the fixture 100, the longitudinal axis 102, and the pivoting mechanism 168 relative to the surgical robot 50 and/or the arm 52 of the surgical robot.

Figure 13:
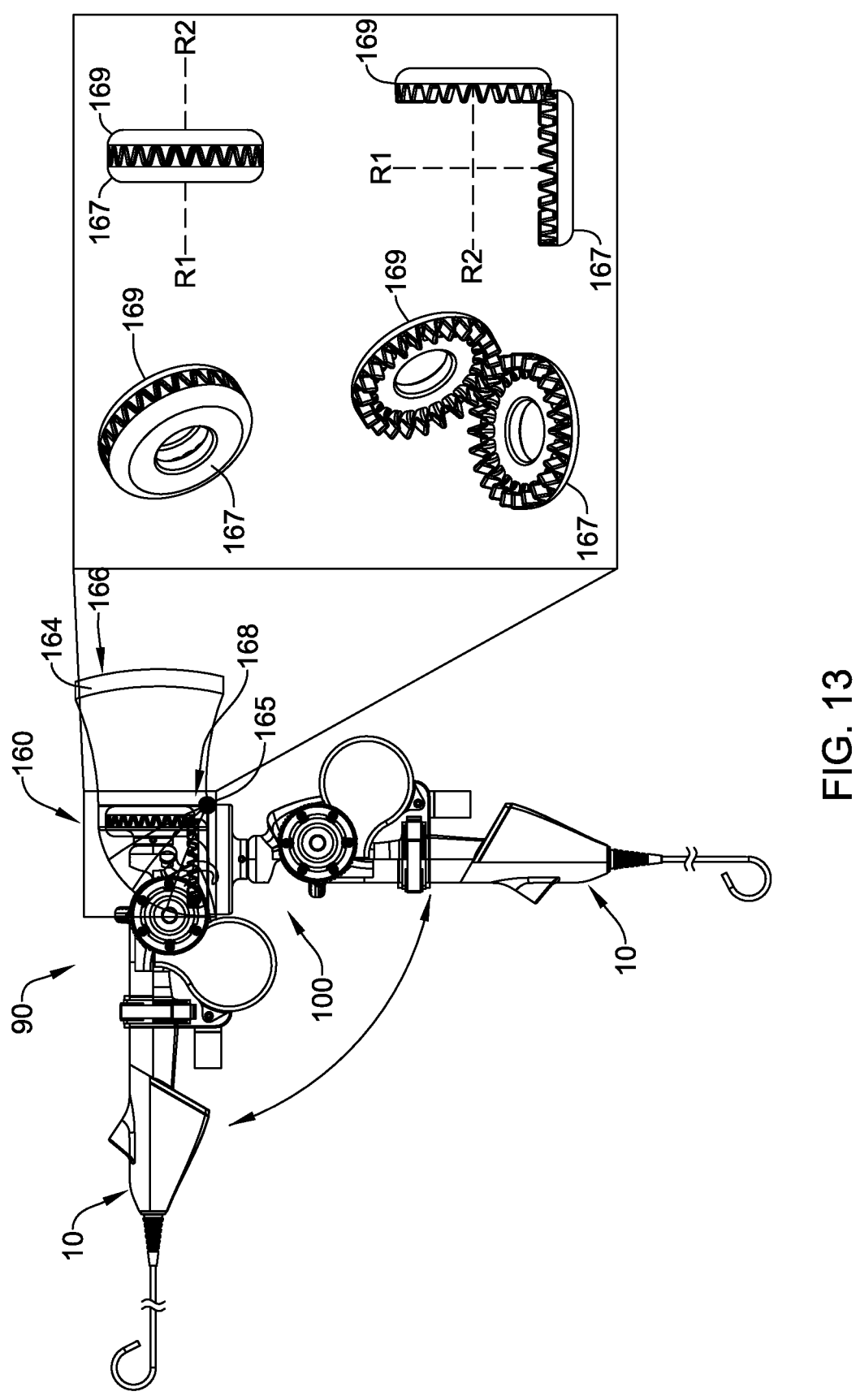
FIG. 13 is a schematic illustration of selected aspects of an alternative configuration of an attachment mechanism for using an endoscope with a surgical robot.

FIG. 13 is a schematic illustration showing selected aspects of another alternative configuration of an attachment mechanism 90 for using an endoscope 10 with a surgical robot 50. The configuration shown in FIG. 13 may be substantially similar to that shown in FIG. 12 in that the mounting structure 160 includes the pivoting mechanism 168 disposed between the mounting plate 164 and the fixture 100. In some embodiments, the fixture 100 may be configured to rotate about its longitudinal axis 102 without rotating the mounting structure 160 and/or the mounting plate 164.

In some embodiments, the mounting structure 160 and/or the pivoting mechanism 168 of FIG. 13 may include a hinge 165 and a first gear 167 engaged with a second gear 169 within the pivoting mechanism 168 at an engagement point. In at least some embodiments, the hinge 165 may be offset from the engagement point.

The first gear 167 and the second gear 169 of the mounting structure 160 and/or the pivoting mechanism 168 may be configured to rotate the fixture 100 about its longitudinal axis 102 without rotating the mounting structure 160 and/or the mounting plate 164 in the first position and in the second position. Function may be similar to the attachment mechanisms shown in FIGS. 9-11 while retaining the ability to selectively position the fixture 100 and/or the handle 20 of the endoscope 10 disposable therein relative to the mounting plate 164, the surgical robot 50, and/or the arm 52 of the surgical robot 50 in one of two or more orientations (e.g., the ability to pivot the fixture 100).

In at least some embodiments, the first gear 167 and the second gear 169 of the mounting structure 160 and/or the pivoting mechanism 168 may be crown gears that permit engagement in a plurality of angles between the first gear 167 and the second gear 169. The first gear 167 and the second gear 169 of the mounting structure 160 and/or the pivoting mechanism 168 may be configured to rotate the fixture 100 about its longitudinal axis 102 in the first position, the second position, and/or any intermediate positions between the first position and the second position.

In some embodiments, the first gear 167 may have a first rotational axis R1, and the second gear 169 may have a second rotational axis R2. In some embodiments, the first rotational axis R1 may intersect with the second rotational axis R2. In some embodiments, the first rotational axis R1 may be oriented coaxially with the second rotational axis R2 in the first position. In some embodiments, the first rotational axis R1 may be oriented generally perpendicular to the second rotational axis R2 in the second position. In some embodiments, the first rotational axis R1 may be oriented at an oblique angle to the second rotational axis R2 in any intermediate positions between the first position and the second position.

FIGS. 14A-14D schematically illustrate the concept of a universal attachment mechanism for using and/or attaching any one of a plurality of endoscopes with the surgical robot 50. In some embodiments, the fixture of the universal attachment mechanism may be configured to receive the handle of any one of, and/or of each of, the plurality of endoscopes in accordance with the attachment mechanism(s) and/or the fixture 100 disclosed herein. In some embodiments, the fixture of the universal attachment mechanism may be configured to receive the handles of each of the plurality of endoscopes without further modification.

In some embodiments, the universal attachment mechanism for using any one of the plurality of endoscopes with the surgical robot 50 may include a fixture configured to receive a handle of the any one of the plurality of endoscopes such that a longitudinal axis of the handle is oriented parallel with a longitudinal axis of the fixture and an elongate shaft of the endoscope extends distally away from the fixture, and a mounting structure secured to the fixture. The mounting structure may be configured to attach the fixture to the surgical robot. The fixture may include a retaining mechanism configured to releasably secure the handle within the fixture. The fixture may include a first motor operably coupled to a first drive mechanism, the first drive mechanism being configured to engage the handle to operate a deflection mechanism of the any one of the plurality of endoscopes. Other structures, elements, and/or features disclosed herein are also contemplated for use with the universal attachment mechanism.

Figures 14A, 14B, 14C, 14D:
FIGS. 14A-14D schematically illustrate a universal attachment mechanism for using any one of a plurality of endoscopes with a surgical robot.
Figures 15A, 15B, 15C:
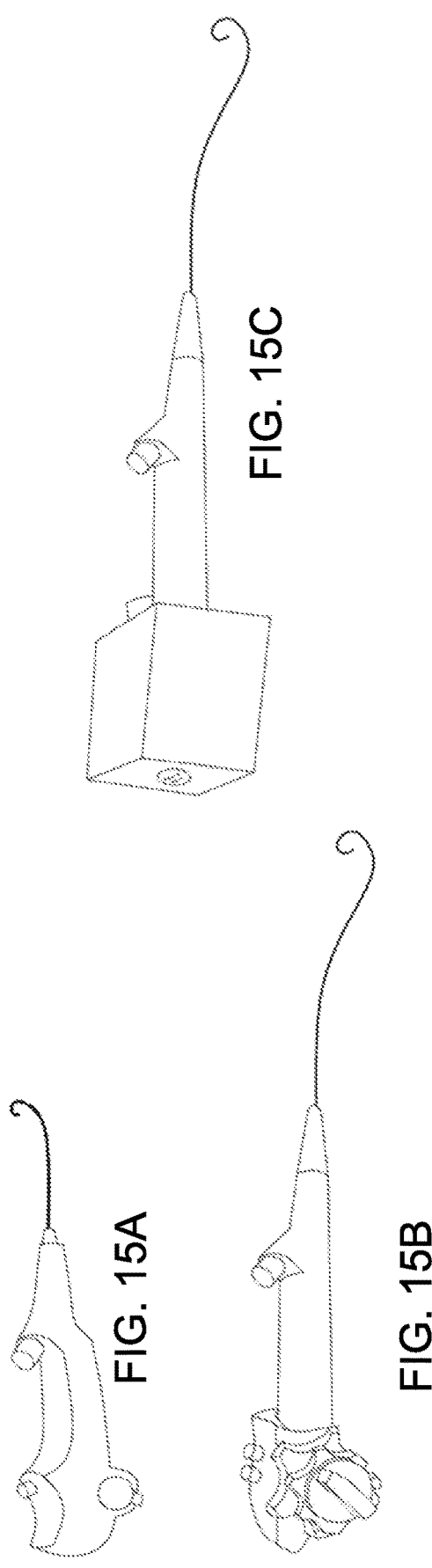
FIGS. 15A-15C schematically illustrate additional examples of endoscopes of the plurality of endoscopes of FIG. 14.

In some embodiments, the fixture of the universal attachment mechanism may be configured to receive the handles of a standard ureteroscope (e.g., FIG. 1, FIG. 14A), a motorized ureteroscope (e.g., FIG. 14B), and a standard ureteroscope including a powered attachment (e.g., FIG. 14C). In some embodiments, the universal attachment mechanism may include a vertical attachment accessory (e.g., FIG. 14D). In some embodiments, the universal attachment mechanism may be configured to receive and/or attach to the surgical robot 50 other types of endoscopes and/or other endoscope handle designs. FIGS. 15A-15C schematically illustrate some examples of additional endoscopes and/or endoscope handle designs that may be usable with the universal attachment mechanism, including but not limited to, an endoscope having a single-axis deflectable tip (e.g., FIG. 15A) and a relatively simple handle, an endoscope having a multi-axis deflectable tip (e.g., FIG. 15B) and a more complex handle, and/or an endoscope having a powered and/or motorized module attached and/or integrated to the handle and configured to operate the deflectable tip (e.g., FIG. 15C). Other configurations are also contemplated.

Figure 16:
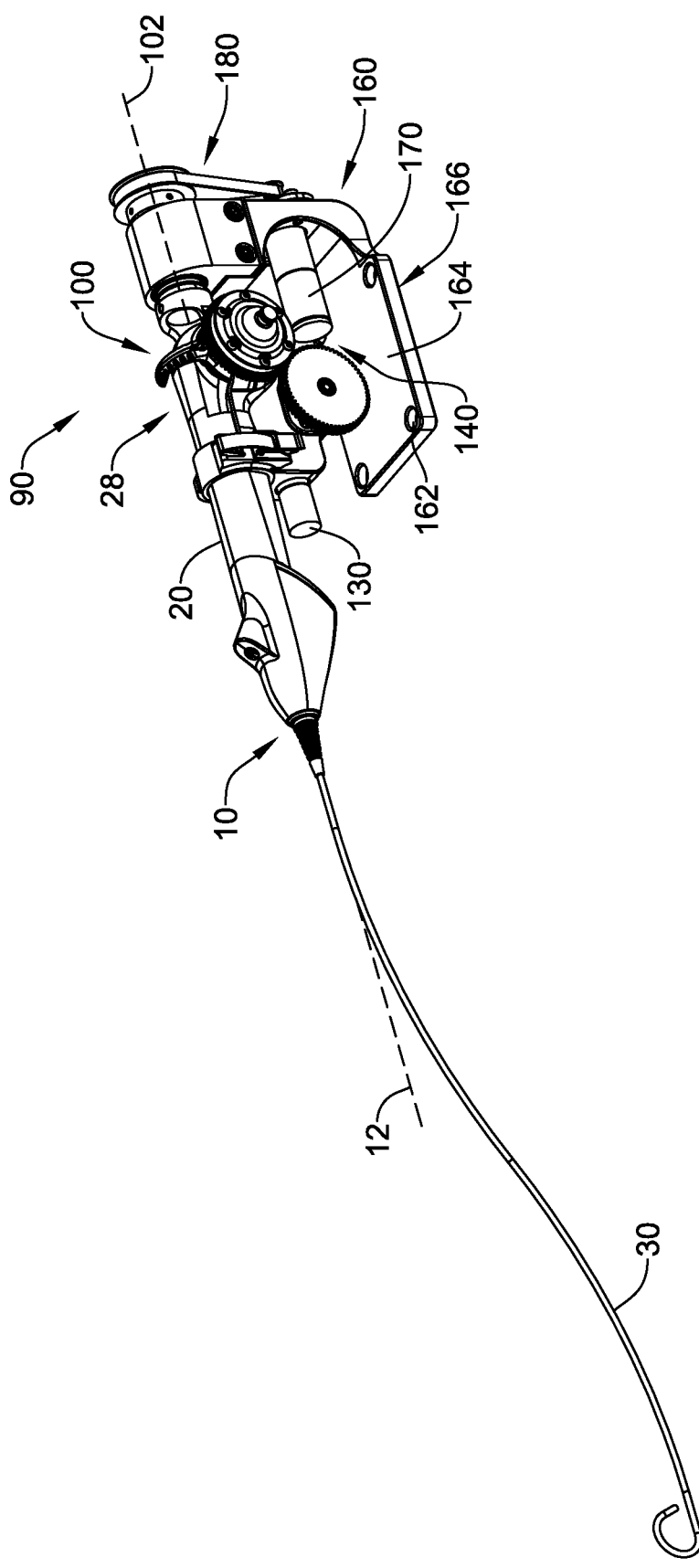
FIG. 16 is a schematic illustration of selected aspects of an alternative configuration of an attachment mechanism for using an endoscope with a surgical robot and/or a linear advancement device.
Figure 31:
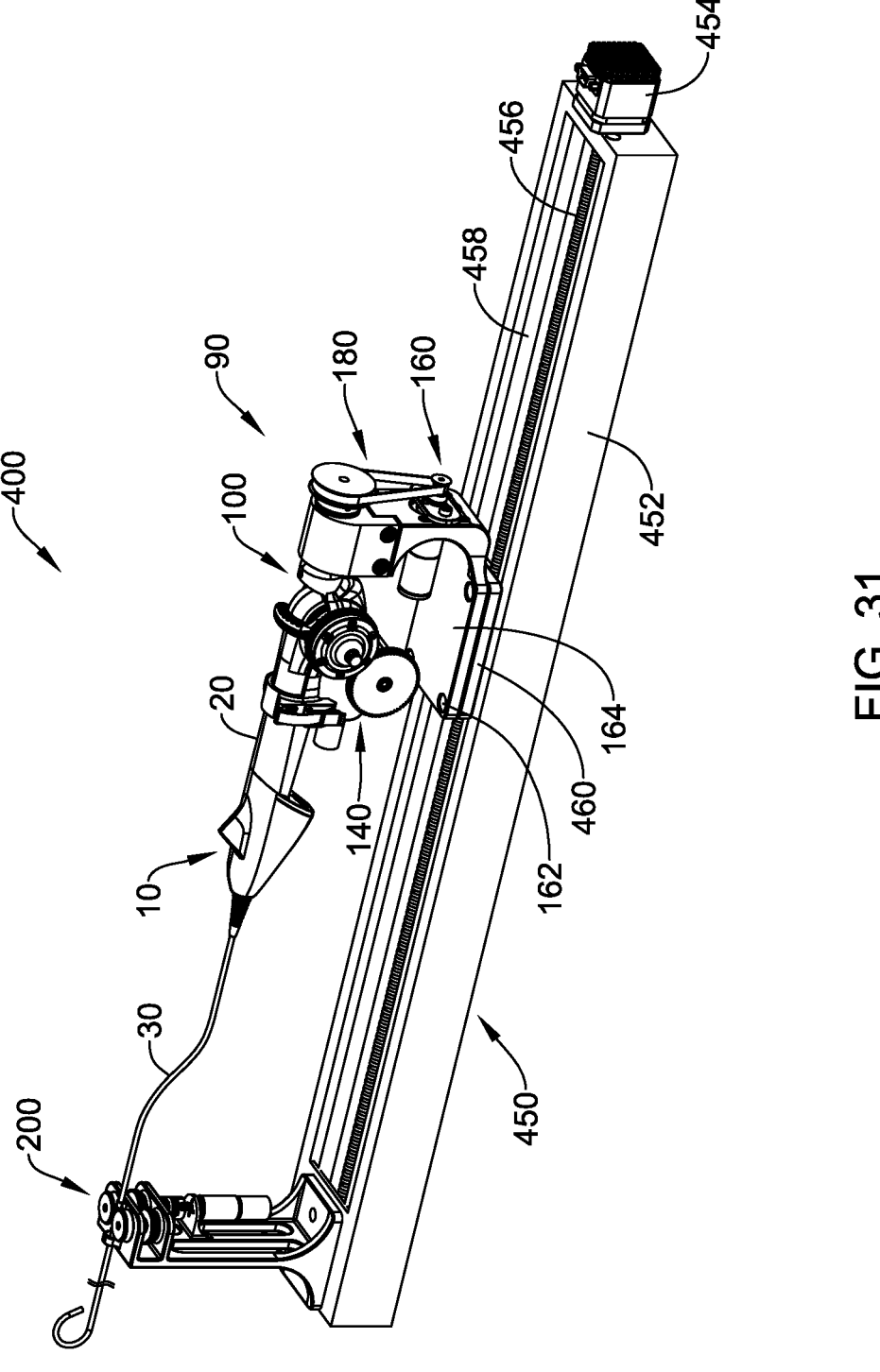
FIG. 31 illustrates selected aspects of a surgical system including a linear advancement device and a motorized introducer apparatus.

FIG. 16 is a schematic illustration of selected aspects of an alternative configuration of an attachment mechanism 90 for using an endoscope 10 with a surgical robot 50 and/or a linear advancement device 450 (e.g., FIG. 31). The attachment mechanism 90 of FIG. 16 may be substantially similar to that illustrated in FIGS. 9 and 11, and thus the same reference numbers and description herein also apply and are not repeated in the interest of brevity. Compared to FIGS. 9 and 11, some details related to form and/or shape of the mounting plate 164 may be different in FIG. 16. For example, in some embodiments, the plurality of apertures 162 may be arranged in a different pattern and/or may include a different quantity of apertures. In some embodiments, the structure for securing the second motor 170 to the mounting structure 160 may be different. Other configurations are also contemplated. In some embodiments, the attachment mechanism 90 of FIG. 16 may be configured for using the endoscope 10 with a linear advancement device 450 (e.g., FIG. 31), as discussed herein, instead of with a multi-axis surgical robot.

Figure 17:
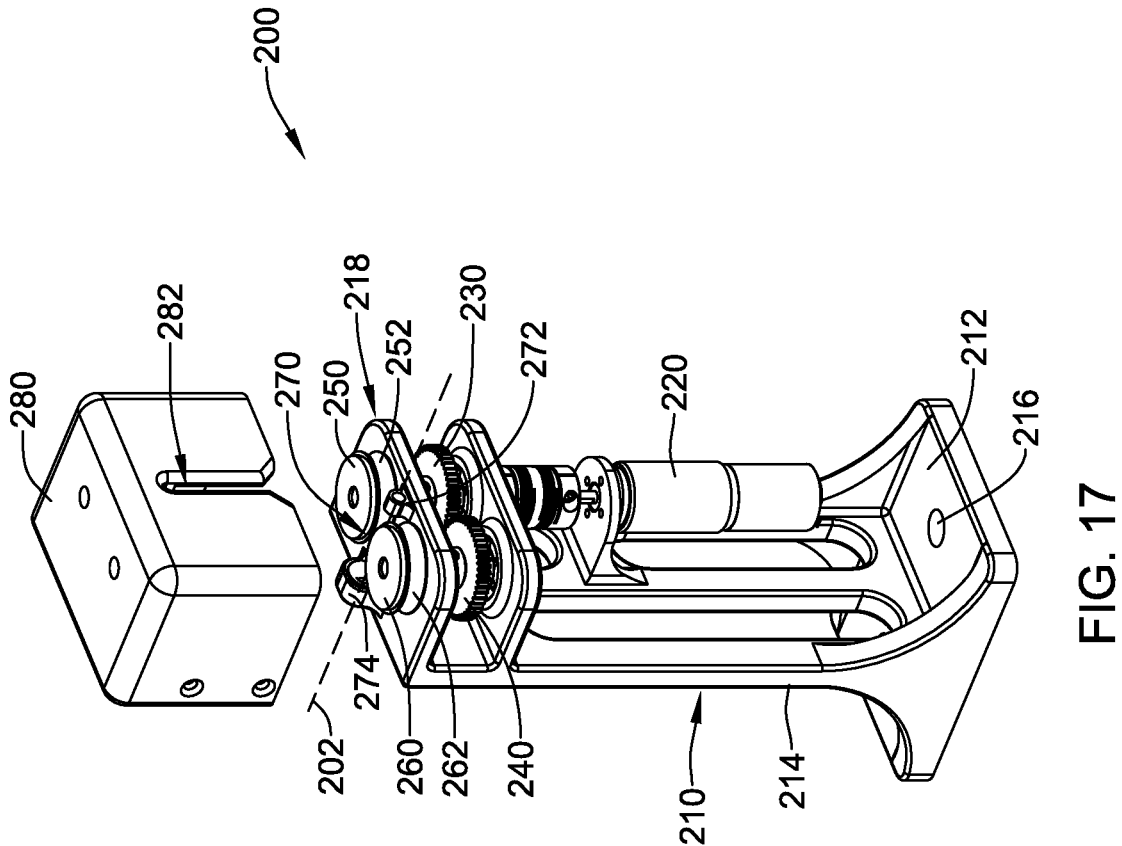
FIG. 17 illustrates selected aspects of a motorized introducer apparatus.

In some situations, navigating the endoscope 10 with the surgical robot 50 and/or the arm 52 of the surgical robot 50 into the patient in a stable and precise manner may be challenging because of the flexible nature of the elongate shaft 30, which may bend, deflect, and/or buckle when encountering opposing forces. When manually inserting the endoscope 10 into the patient, the physician uses two hands—one hand on the handle 20 to control rotation of the endoscope 10 and/or to control the deflection mechanism 28 for actuating the deflectable distal tip 32, and a second hand on the elongate shaft 30. The physician's actions with the second hand reduces the opportunity for buckling of the elongate shaft 30. In some situations, a surgical system 400 (e.g., FIGS. 28-31) may include a motorized introducer apparatus 200 for translating the elongate shaft 30 of the endoscope 10 relative to the patient, one example of which is shown in FIG. 17. The motorized introducer apparatus 200 may be used as a stabilizer and/or as an alternative to using the second hand of the physician. The motorized introducer apparatus 200 may be configured to translate the elongate shaft 30 axially and/or longitudinally toward and/or away from the patient.

In some embodiments, the motorized introducer apparatus 200 may include a body 210. In some embodiments, the body 210 may form and/or function as a stand. In some embodiments, the body 210 may be a substantially rigid structure configured to support other elements and/or components of the motorized introducer apparatus 200. In some embodiments, the body 210 may be formed using one or more of a variety of processes such as casting, molding, machining, welding, etc. Some suitable but non-limiting materials for the body 210, and/or components or elements thereof, for example metallic materials, polymeric materials, composite materials, etc. and/or combinations thereof, are described below.

In some embodiments, the body 210 may include a base portion 212 and an upright portion 214 extending upward from the base portion 212. Other configurations are also contemplated. In some embodiments, the body 210 and/or the base portion 212 may include at least one mounting hole 216 for securing the motorized introducer apparatus 200 and/or the body 210 relative to the patient, a surgical bed, and/or as described herein.

In some embodiments, the motorized introducer apparatus 200 may include a motor 220 fixedly attached to the body 210. In some embodiments, the motor 220 may be fixedly attached to the upright portion 214. In some embodiments, the motorized introducer apparatus 200 may include a drive gear 230 operatively coupled to the motor 220. In some embodiments, the motorized introducer apparatus 200 may include a drive wheel 250 operatively coupled to the drive gear 230. In some embodiments, the motorized introducer apparatus 200 may include a support wheel 260 positioned proximate and/or adjacent the drive wheel 250 such that the drive wheel 250 and the support wheel 260 may be configured to engage the elongate shaft 30 of the endoscope 10 when the elongate shaft 30 is disposed between the drive wheel 250 and the support wheel 260. The motor 220 may be configured to drive and/or rotate the drive gear 230 and the drive wheel 250. The drive gear 230 and the drive wheel 250 may be configured to translate the elongate shaft 30 relative to the patient and/or through the motorized introducer apparatus 200. In some embodiments, the support wheel 260 may be configured to function solely as a guide and/or as a stabilizer for the elongate shaft 30.

In some embodiments, the motorized introducer apparatus 200 may optionally include a support gear 240 engaged with the drive gear 230. Where present, the support gear 240 may be operatively coupled to the support wheel 260. As the motor 220 drives and/or rotates the drive gear 230, the support gear 240 may be driven or rotated via engagement with the drive gear 230, thereby driving and/or rotating the support wheel 260. Accordingly, in some embodiments, the support gear 240 and the support wheel 260 may be configured to actively aid in translating the elongate shaft 30 relative to the patient and/or through the motorized introducer apparatus 200. Other configurations are also contemplated.

In some embodiments, the motorized introducer apparatus 200 may include a plurality of drive gears and a plurality of drive wheels. In some embodiments, the motorized introducer apparatus 200 may include a plurality of support gears and a plurality of support wheels. Various combinations of the features discussed herein are also contemplated.

In some embodiments, the elongate shaft 30 of the endoscope 10 may be disposable between the drive wheel 250 and the support wheel 260 at an engagement location 270 such that the elongate shaft 30 is configured to selectively move longitudinally and/or axially along an axis of movement 202 through the motorized introducer apparatus 200 when engaged with the drive wheel 250 and the support wheel 260.

In some embodiments, the drive wheel 250 may include at least one soft polymeric drive ring 252 extending around a circumference of the drive wheel 250. In some embodiments, the drive wheel 250 may include two soft polymeric drive rings extending around the circumference of the drive wheel 250. In some embodiments, the two soft polymeric drive rings may be spaced apart from each other. For example, a first drive ring of the two soft polymeric drive rings may be positioned a greater distance from the motor 220 than a second drive ring of the two soft polymeric drive rings. Other configurations are also contemplated. In some embodiments having a plurality of drive wheels, each drive wheel may include at least one soft polymeric drive ring extending around the circumference of the drive wheel. In some embodiments having a plurality of drive wheels, each drive wheel may include two soft polymeric drive rings extending around the circumference of the drive wheel. Other configurations are also contemplated.

In some embodiments, the support wheel 260 may include at least one soft polymeric support ring 262 extending around a circumference of the support wheel 260. In some embodiments, the support wheel 260 may include two soft polymeric support rings extending around the circumference of the support wheel 260. In some embodiments, the two soft polymeric support rings may be spaced apart from each other. For example, a first support ring of the two soft polymeric support rings may be positioned a greater distance from the motor 220 than a second support ring of the two soft polymeric support rings. Other configurations are also contemplated. In some embodiments having a plurality of support wheels, each support wheel may include at least one soft polymeric support ring extending around the circumference of the support wheel. In some embodiments having a plurality of support wheels, each support wheel may include two soft polymeric support rings extending around the circumference of the support wheel. Other configurations are also contemplated.

In some embodiments, the at least one soft polymeric drive ring 252 and the at least one soft polymeric support ring 262, when engaged with the elongate shaft 30 of the endoscope 10 at the engagement location 270, may cooperate to longitudinally and/or axially move and/or translate the elongate shaft 30 of the endoscope 10 along the axis of movement 202 while permitting rotation of the elongate shaft 30 of the endoscope 10 about and/or around the axis of movement 202.

In some embodiments, the at least one soft polymeric drive ring 252 and the at least one soft polymeric support ring 262 may be generally u-shaped with raised edges and a recessed center portion such that the elongate shaft 30 may be received within the recessed center portion and/or between the raised edges. In some embodiments, the at least one soft polymeric drive ring 252 and the at least one soft polymeric support ring 262 may each be and/or include an O-ring such that the elongate shaft 30 may be engageable with each O-ring at the engagement location 270. Other configurations, including combinations thereof, are also contemplated.

In some embodiments, the motorized introducer apparatus 200 and/or the body 210 may include at least one lateral flange 218 extending from the upright portion 214. In some embodiments, the drive gear 230, the support gear 240, the drive wheel 250, and/or the support wheel 260 may be coupled to the at least one lateral flange 218. In some embodiments, the drive gear 230 and the support gear 240, where present, may be disposed between adjacent lateral flanges of the at least one lateral flange 218. In some embodiments, the drive wheel 250 and the support wheel 260 may be disposed over and/or above the at least one lateral flange 218 opposite the base portion 212.

In some embodiments, the drive wheel 250 and/or the support wheel 260 may be laterally fixed in position relative to the body 210 and/or the at least one lateral flange 218. The drive wheel 250 and/or the support wheel 260 may be rotatable relative to the body 210 and/or the at least one lateral flange 218.

In some embodiments, the body 210 and/or the at least one lateral flange 218 may include a proximal guide ring 272 disposed proximal of the engagement location 270 and a distal guide ring 274 disposed distal of the engagement location 270. In some embodiments, the proximal guide ring 272 and the distal guide ring 274 may be fixedly attached to the body 210 and/or the at least one lateral flange 218. In some embodiments, the proximal guide ring 272 and the distal guide ring 274 may be monolithic with and/or may be integrally formed with the body 210 and/or the at least one lateral flange 218. In some embodiments, the proximal guide ring 272 and the distal guide ring 274 may be disposed and/or oriented coaxial with the axis of movement 202. In some embodiments, the proximal guide ring 272 and the distal guide ring 274 may extend from the at least one lateral flange 218 in a direction opposite the base portion 212 from the at least one lateral flange 218. In some embodiments, the proximal guide ring 272 and the distal guide ring 274 may extend upward from the at least one lateral flange 218.

In some embodiments, the motorized introducer apparatus 200 may include a cover 280 securable and/or attachable to the body 210 and/or the upright portion 214. In some embodiments, the cover 280 may be securable and/or attachable to the body 210 and/or the upright portion 214 over the drive gear 230, the support gear 240, the drive wheel 250, and/or the support wheel 260. In some embodiments, the cover 280 may be securable and/or attachable to the body 210 and/or the upright portion 214 over the engagement location 270. In some embodiments, the cover 280 may include a proximal opening 282 and/or a distal opening (not shown) such that when the cover 280 is secured and/or attached to the body 210 and/or the upright portion 214, the engagement location 270 may be in communication with and/or may be accessible from outside of the cover 280.

In some embodiments, when the cover 280 is secured and/or attached to the body 210 and/or the upright portion 214, the elongate shaft 30 of the endoscope 10 may be positionable through the motorized introducer apparatus 200 and/or the cover 280. In at least some embodiments, the elongate shaft 30 of the endoscope 10 may be positionable within and/or through the proximal guide ring 272, the engagement location 270, and the distal guide ring 274, and the cover 280 may be subsequently secured and/or attached to the body 210 and/or the upright portion 214 such that the elongate shaft 30 of the endoscope 10 extends through the proximal opening 282 and the distal opening of the cover 280.

While not explicitly necessary for the motorized introducer apparatus 200 to function properly, the cover 280 may be provided to eliminate one or more pinch points and/or to reduce contamination and/or interference with the drive gear 230, the support gear 240, the drive wheel 250, and/or the support wheel 260.

In some embodiments, the motorized introducer apparatus 200 may be controlled and/or operated individually, independently of any other apparatus, and/or as a standalone device. In some embodiments, the motorized introducer apparatus 200 may be controlled and/or operated in conjunction with one or more other medical devices or other apparatuses as one element or component of the surgical system 400 (e.g., FIGS. 28-31). Other configurations and/or combinations thereof are also contemplated.

Figure 18:
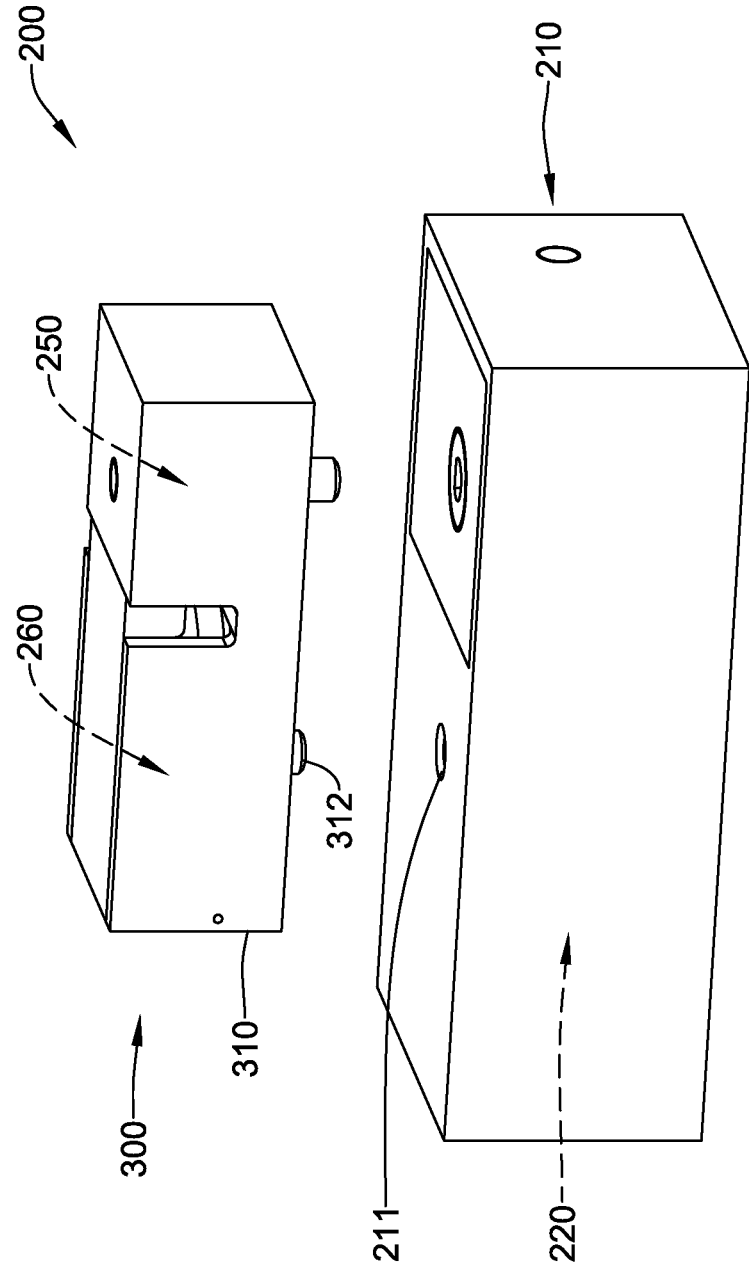
FIG. 18 illustrates selected aspects of a motorized introducer apparatus.
Figure 25:
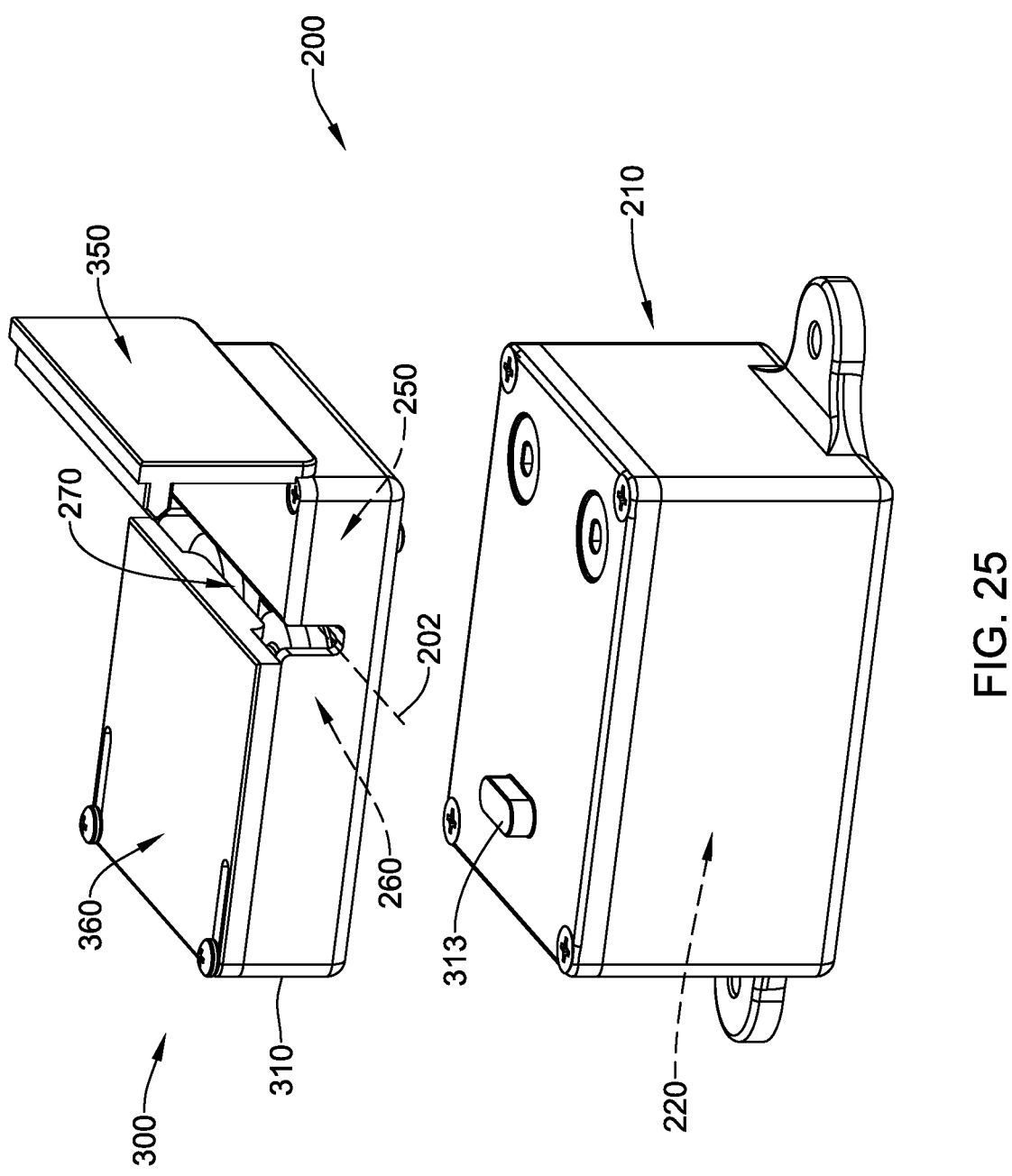
FIGS. 25-27 illustrate selected aspects of a configuration of the motorized introducer apparatus of FIG. 18.

In some embodiments, the motorized introducer apparatus 200 may comprise a longitudinal motion unit 300 including a second body 310 removably coupled to the body 210, as shown in FIG. 18. In some embodiments, the drive wheel 250 and the support wheel 260 may be disposed within the second body 310. In some embodiments, the second body 310 may be nonrotatable relative to the body 210 when the second body 310 is removably coupled to and/or engaged with the body 210. In some embodiments, the second body 310 may include a projection 312 extending from an outer surface of the second body 310, as seen in FIGS. 18-24, and configured to engage a recess or an aperture 211 formed in the body 210, as seen in FIG. 18. In some embodiments, the body 210 may include a projection 313 extending from an outer surface of the body 210 and configured to engage a recess or an aperture (not shown) formed in the second body 310, as seen in FIG. 25. Other configurations are also contemplated. In at least some embodiments, the longitudinal motion unit 300, the second body 310, and/or components disposed therein and/or thereon may be disposable (e.g., single use) and the body 210 may be reusable. In one example, during use, the body 210 may be protected by a surgical drape. In another example, the body 210 may be sterilizable for re-use.

Figures 22, 23, 24:
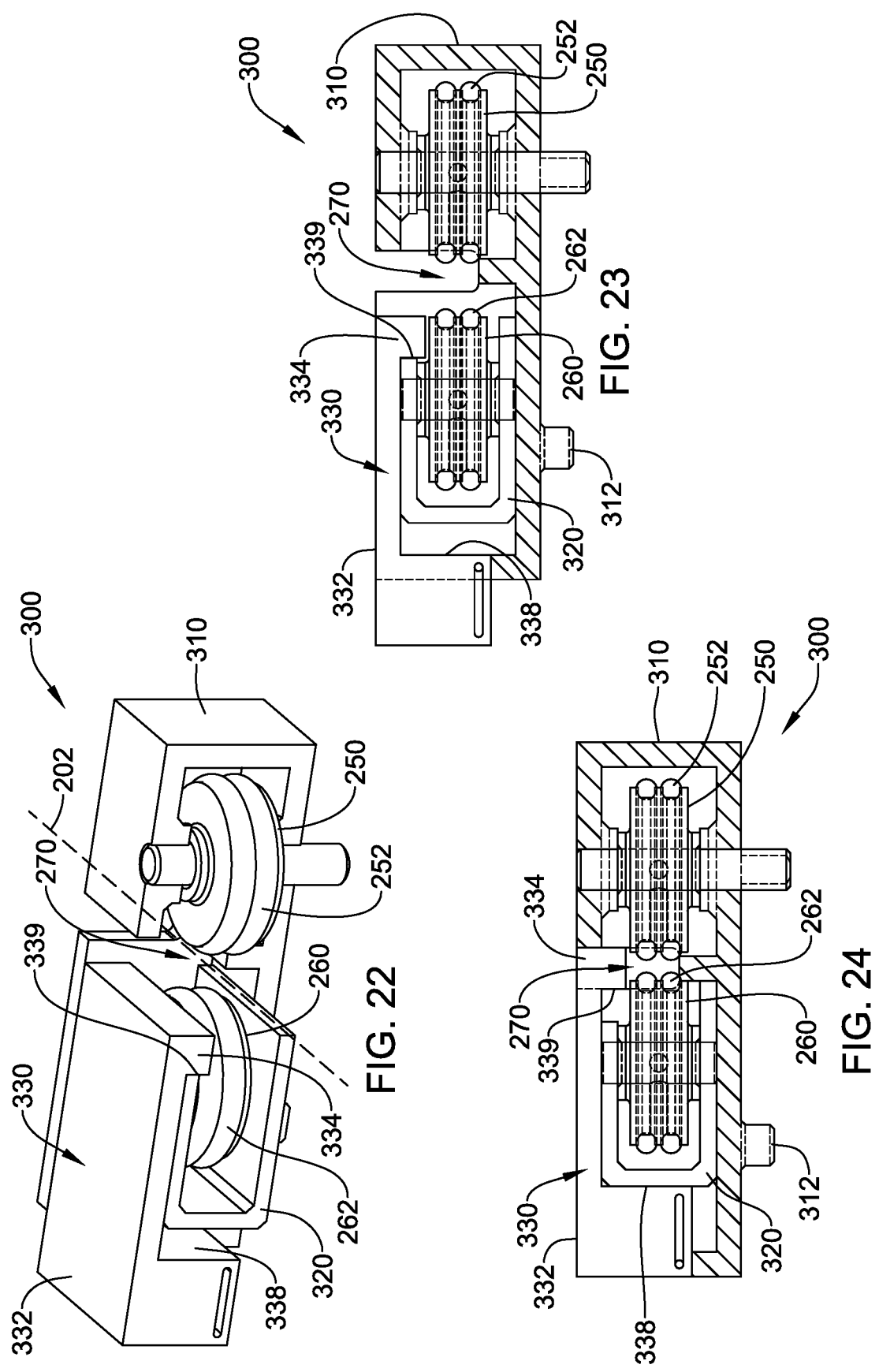
FIGS. 22-24 illustrate selected aspects of a configuration of the motorized introducer apparatus of FIG. 18.
Figures 26, 27:
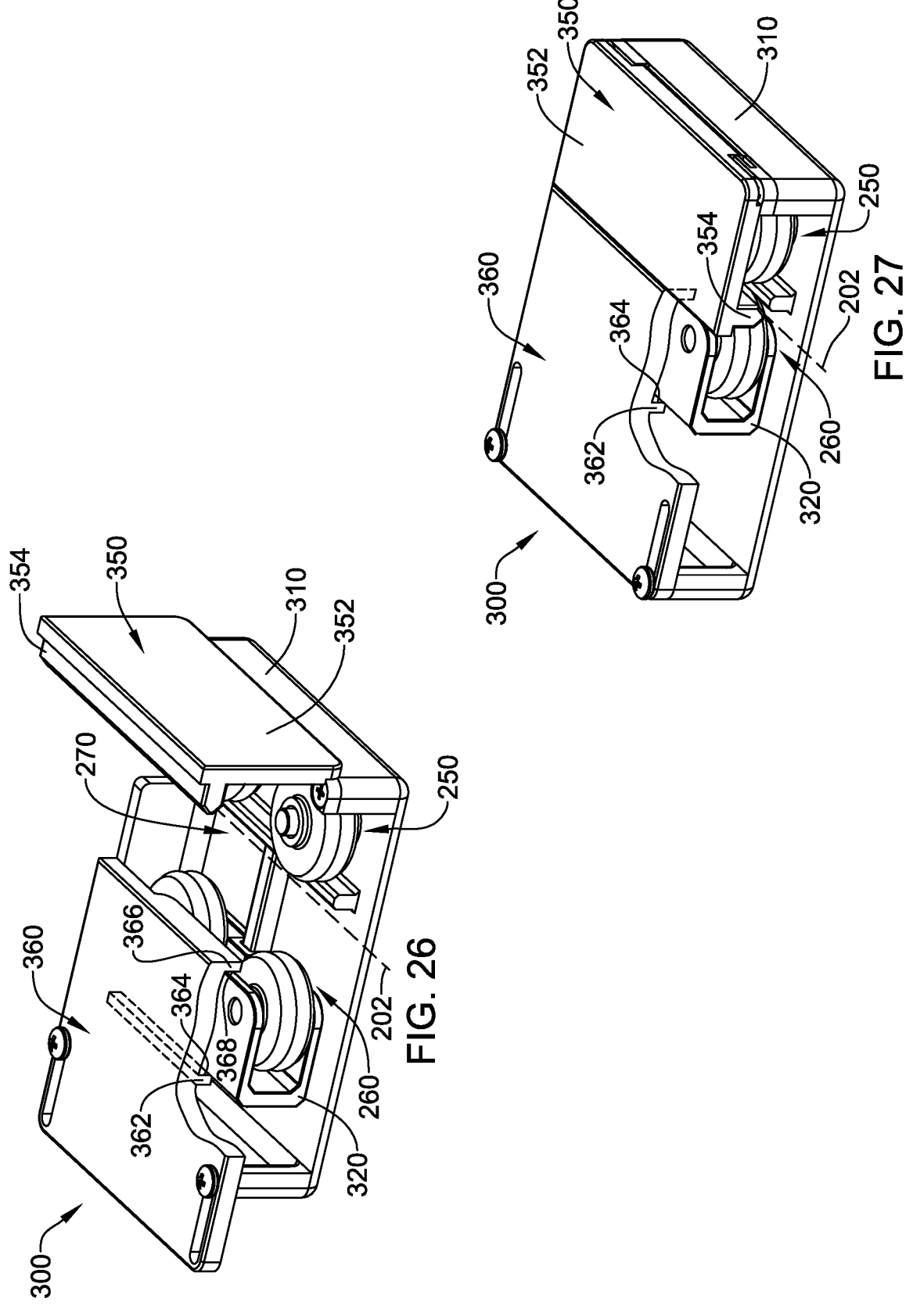

In some embodiments, the support wheel 260 may be movable within the second body 310, as shown in FIGS. 19-27, between an engaged position (e.g., FIGS. 21, 24, 27) and a disengaged position (e.g., FIGS. 20, 23, 26). In the engaged position, the support wheel 260 may be in contact with and/or may be engaged with the elongate shaft 30 of the endoscope 10 when the endoscope 10 is disposed at and/or within the engagement location 270. In the disengaged position, the support wheel 260 may be spaced apart from and/or may be disengaged from the elongate shaft 30 of the endoscope 10 when the endoscope 10 is disposed at and/or within the engagement location 270.

In some embodiments, the drive wheel 250 may be laterally fixed in position within and/or relative to the second body 310. The drive wheel 250 may be rotatable relative to the second body 310. In at least some embodiments, the support wheel 260 may be disposed within and/or may be coupled to a slider 320 configured to move laterally within the second body 310. As such, the slider 320 may be configured to move the support wheel 260 within the second body 310 and/or the support wheel 260 may be configured to move along with and/or simultaneously with the slider 320. The support wheel 260 may be rotatable with respect to the slider 320. The support wheel 260 may be otherwise fixed in position relative to the slider 320. In at least some embodiments, the support wheel 260 and/or the slider 320 may be movable within the second body 310, as shown in FIGS. 19-27, between the engaged position (e.g., FIGS. 21, 24, 27) and the disengaged position (e.g., FIGS. 20, 23, 26)

In some embodiments, the longitudinal motion unit 300 may include a cover 330 movable relative to the second body 310 between an open position (e.g., FIGS. 20, 23) and a closed position (e.g., FIGS. 21, 24). In some embodiments, the cover 330 may be pivotably coupled to the second body 310, as seen in FIGS. 19-21. In some embodiments, the cover 330 may be slidably coupled to the second body 310, as seen in FIGS. 22-24. Other configurations are also contemplated.

In some embodiments, in the closed position of the cover 330, the cover 330 may be configured to maintain, retain, and/or lock the elongate shaft 30 of the endoscope 10 within the engagement location 270. In some embodiments, the cover 330 may include an extension 334 extending generally perpendicular to and opposite from an upper surface 332 of the cover 330. In some embodiments, in the closed position of the cover 330, the extension 334 may extend into and/or toward the engagement location 270. In some embodiments, in the open position of the cover 330, the elongate shaft 30 of the endoscope 10 may be removable from the engagement location 270 in a direction noncoaxial with the axis of movement 202. In the closed position of the cover 330, the support wheel 260 may be disposed a first distance from the drive wheel 250, and in the open position of the cover 330, the support wheel 260 may be disposed a second distance from the drive wheel 250. The second distance may be greater than the first distance.

In some embodiments, the slider 320 and/or the support wheel 260 may be biased toward the disengaged position when the cover 330 is moved toward and/or to the open position. In some embodiments, the slider 320 and/or the support wheel 260 may be biased toward the disengaged position by the cover 330 when the cover 330 is moved toward and/or to the open position. In some embodiments, the slider 320 and/or the support wheel 260 may be biased toward the engaged position when the cover 330 is moved toward and/or to the closed position. In some embodiments, the slider 320 and/or the support wheel 260 may be biased toward the engaged position by the cover 330 when the cover 330 is moved toward and/or to the closed position.

In some embodiments, the cover 330 may include an angled surface 336 configured to engage the slider 320 as the cover 330 is moved from the open position toward and/or to the closed position. Engagement of the angled surface 336 of the cover 330 with the slider 320 as the cover 330 is moved toward and/or to the closed position may urge, bias, and/or move the slider 320 and/or the support wheel 260 toward the engaged position, as seen in FIGS. 20-21.

In some embodiments, the cover 330 may include a first lateral surface 338 configured to engage the slider 320 as the cover 330 is moved from the open position toward and/or to the closed position. Engagement of the first lateral surface 338 of the cover 330 with the slider 320 as the cover 330 is moved toward and/or to the closed position may urge, bias, and/or move the slider 320 and/or the support wheel 260 toward the engaged position, as seen in FIG. 24. In some embodiments, the cover 330 and/or the extension 334 may include a second lateral surface 339 facing toward the first lateral surface 338, the second lateral surface 339 being configured to engage the slider 320 as the cover 330 is moved from the closed position toward and/or to the open position. Engagement of the second lateral surface 339 of the cover 330 with the slider 320 as the cover 330 is moved toward and/or to the open position may urge, bias, and/or move the slider 320 and/or the support wheel 260 toward the disengaged position, as seen in FIG. 23.

In some embodiments, as seen in FIGS. 25-27, the longitudinal motion unit 300 may include a first cover 350 pivotable relative to the second body 310 between an open position and a closed position, and the longitudinal motion unit 300 may include a second cover 360 slidable relative to the second body 310 between an open position and a closed position.

In some embodiments, in the closed position of the first cover 350, the first cover 350 may be configured to maintain, retain, and/or lock the elongate shaft 30 of the endoscope 10 within the engagement location 270. In some embodiments, the first cover 350 may include a first extension 354 extending generally perpendicular to and opposite from an upper surface 352 of the first cover 350. In some embodiments, the first extension 354 may extend in a first direction from the first cover 350 when the first cover 350 is in the closed position. In some embodiments, in the closed position of the first cover 350, the first extension 354 and/or the first direction may extend into and/or toward the engagement location 270. In some embodiments, in the open position of the first cover 350, the elongate shaft 30 of the endoscope 10 may be removable from the engagement location 270 in a direction noncoaxial with the axis of movement 202.

In the closed position of the second cover 360, the support wheel 260 may be disposed a first distance from the drive wheel 250, and in the open position of the second cover 360, the support wheel 260 may be disposed a second distance from the drive wheel 250. The second distance may be greater than the first distance.

In some embodiments, the slider 320 and/or the support wheel 260 may be biased toward the disengaged position when the second cover 360 is moved toward and/or to the open position. In some embodiments, the slider 320 and/or the support wheel 260 may be biased toward the disengaged position by the second cover 360 when the second cover 360 is moved toward and/or to the open position. In some embodiments, the slider 320 and/or the support wheel 260 may be biased toward the engaged position when the second cover 360 is moved toward and/or to the closed position. In some embodiments, the slider 320 and/or the support wheel 260 may be biased toward the engaged position by the second cover 360 when the second cover 360 is moved toward and/or to the closed position.

In some embodiments, the second cover 360 may include a second extension 362 extending generally perpendicular to and opposite from an upper surface 361 of the second cover 360. In some embodiments, the second extension 362 may be disposed at and/or may extend from a medial portion of the second cover 360. The second extension 362 may extend in the first direction from the second cover 360. The second cover 360 and/or the second extension 362 may include a first lateral surface 364 configured to engage the slider 320 as the second cover 360 is moved from the open position to the closed position. Engagement of the first lateral surface 364 of the second cover 360 and/or the second extension 362 with the slider 320 as the second cover 360 is moved toward and/or to the closed position may urge, bias, and/or move the slider 320 and/or the support wheel 260 toward the engaged position, as seen in FIG. 27. In some embodiments, the second cover 360 may include a third extension 366 extending generally perpendicular to and opposite from the upper surface 361 of the second cover 360. The third extension 366 may extend in the first direction from the second cover 360. In some embodiments, the second cover 360 and/or the third extension 366 may include a second lateral surface 368 facing toward the first lateral surface 364, the second lateral surface 368 being configured to engage the slider 320 as the second cover 360 is moved from the closed position to the open position. Engagement of the second lateral surface 368 of the second cover 360 and/or the third extension 366 with the slider 320 as the second cover 360 is moved toward and/or to the open position may urge, bias, and/or move the slider 320 and/or the support wheel 260 toward the disengaged position, as seen in FIG. 26.

As discussed herein, in some embodiments, the motorized introducer apparatus 200 may include a plurality of drive wheels and/or a plurality of support wheels. As such, in some embodiments, the longitudinal motion unit 300 may include a plurality of drive wheels and/or a plurality of support wheels disposed therein. The plurality of drive wheels may be laterally fixed in position relative to the second body 310. The plurality of drive wheels may be rotatable relative to the second body 310. The plurality of support wheels may be disposed within and/or coupled to the slider 320. The slider 320 and/or the plurality of support wheels may be laterally movable within the second body 310. Other configurations are also contemplated.

In some embodiments having a plurality of drive wheels, the motorized introducer apparatus 200 may include a plurality of drive gears coupled to and/or disposed within the body 210. In some embodiments, the motorized introducer apparatus 200 may include a plurality of support gears configured to engage the plurality of drive gears. The plurality of support gears may be operatively coupled to the plurality of support wheels. Other configurations are also contemplated.

Figure 28:
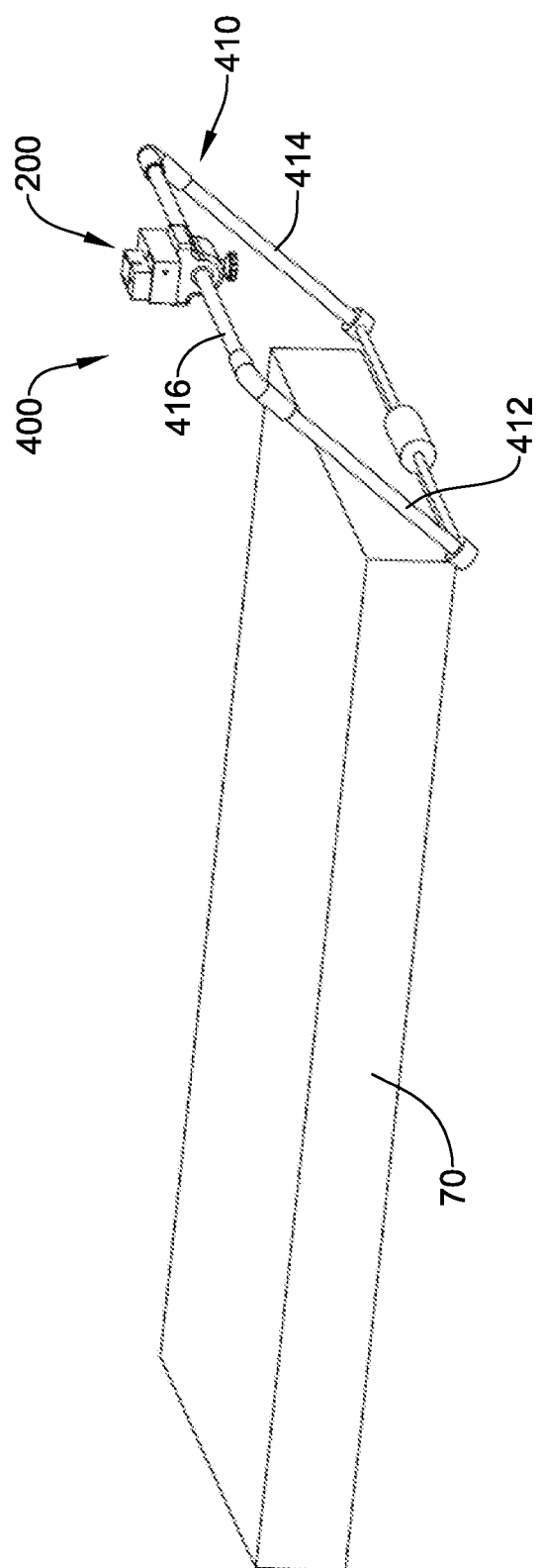
FIG. 28 illustrates selected aspects of a surgical system including a support frame attachable to a surgical bed.
Figure 29:
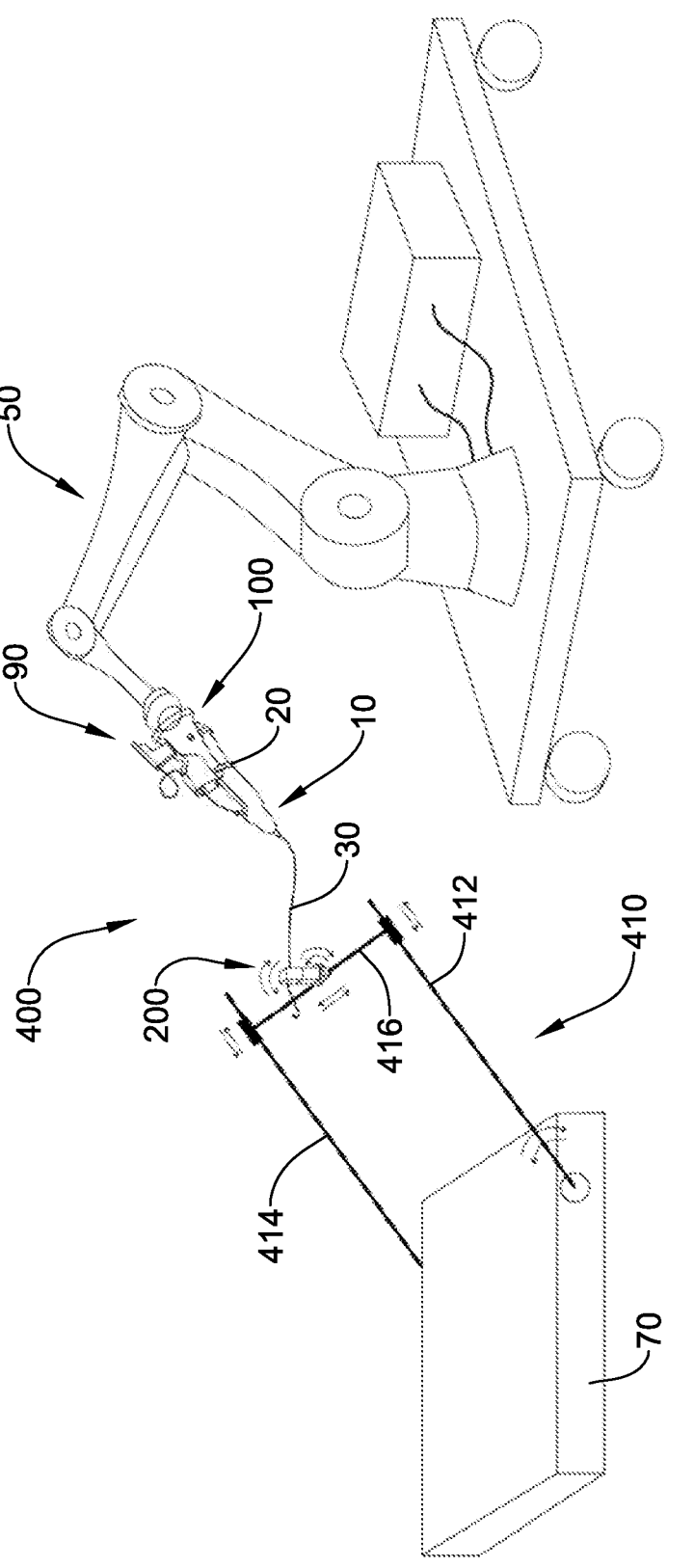
FIG. 29 illustrates selected aspects of a surgical system including a support frame attachable to a surgical bed.
Figure 30:
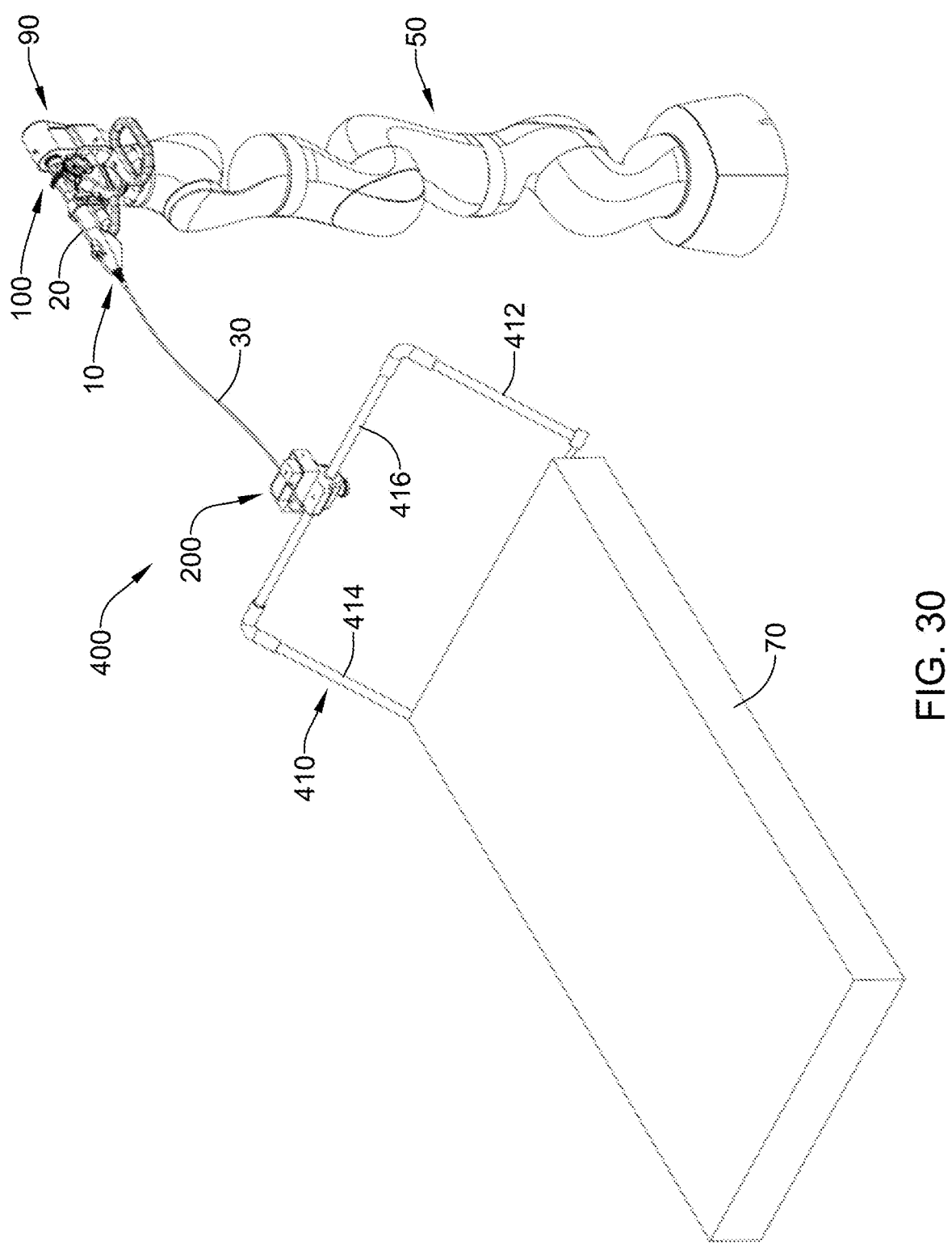
FIG. 30 illustrates selected aspects of a surgical system including a support frame attachable to a surgical bed.

FIGS. 28-30 schematically illustrate selected aspects of a surgical system 400 comprising the motorized introducer apparatus 200, as described herein, and a support frame 410 attachable to a surgical bed 70. In some embodiments, the motorized introducer apparatus 200 may be secured to the support frame 410. In some embodiments, the support frame 410 may be movable relative to the surgical bed 70. In some embodiments, the support frame 410 may be configured to pivot relative to the surgical bed 70. In some embodiments, the support frame 410 may be configured to translate laterally relative to a longitudinal axis of the surgical bed 70.

In some embodiments, the support frame 410 may include a first side support 412, a second side support 414, and a horizontal member 416 extending from the first side support 412 to the second side support 414. In some embodiments, the horizontal member 416 may be fixedly attached to the first side support 412 and the second side support 414. In some embodiments, the horizontal member 416 may be movable along and/or relative to the first side support 412 and the second side support 414.

In some embodiments, the motorized introducer apparatus 200 may be movable relative to the horizontal member 416. In some embodiments, the motorized introducer apparatus 200 may be movable along the horizontal member 416. In some embodiments, the motorized introducer apparatus 200 may be pivotable about the horizontal member 416. Other configurations, including but not limited to combinations thereof, are also contemplated.

In some embodiments, the surgical system 400 may include the attachment mechanism 90 described herein. As discussed herein, the attachment mechanism 90 may be securable and/or attachable to a surgical robot 50. The attachment mechanism 90 may include the fixture 100 configured to receive the handle 20 of the endoscope 10. The motorized introducer apparatus 200 may be configured to advance, retract, and/or translate the elongate shaft 30 of the endoscope 10. The motorized introducer apparatus 200 may be configured to advance, retract, and/or translate the elongate shaft 30 of the endoscope 10 relative to the support frame 410, the surgical bed 70, and/or a patient disposed on the surgical bed 70.

In some embodiments, the motorized introducer apparatus 200 may be configured to advance and/or translate the elongate shaft 30 of the endoscope 10 toward and/or into the patient as the surgical robot 50 moves the handle 20 of the endoscope 10 toward the patient. In some embodiments, the motorized introducer apparatus 200 may be configured to retract and/or translate the elongate shaft 30 of the endoscope 10 away from and/or out of the patient as the surgical robot 50 moves the handle 20 of the endoscope 10 away from the patient. Other configurations are also contemplated.

In some urologic applications of the surgical system 400 shown in FIGS. 28-30, in some embodiments, the patient may be positioned with their feet towards the support frame 410. In some embodiments, the patient's feet may be disposed and/or positioned within stirrups and the elongate shaft 30 of the endoscope 10 may be inserted into the patient's leg or groin. Other configurations are also contemplated. For example, in some other endoscopic procedures, the patient may be positioned with their head towards the support frame 410 and the elongate shaft 30 of the endoscope 10 may be inserted into the patient's neck, shoulder, or arm.

In some embodiments, the surgical system 400 may include a linear advancement device 450, as seen in FIG. 31. In some embodiments, the linear advancement device 450 may include a frame 452. In some embodiments, the linear advancement device 450 may include a motor 454 fixed to the frame 452. In some embodiments, the linear advancement device 450 may include an advancement mechanism 456 disposed within the frame 452 and operatively coupled to the motor 454. In some embodiments, the advancement mechanism 456 may include a drive shaft, a drive belt, a drive chain, a ball screw, a rack and pinion, etc., or other suitable drive means. In some embodiments, the linear advancement device 450 may include at least one guide rail 458 extending longitudinally within the frame 452. In some embodiments, the linear advancement device 450 may include a transport pod 460 operatively coupled to the advancement mechanism 456. In some embodiments, the transport pod 460 may be slidably coupled to the at least one guide rail 458.

In some embodiments, the transport pod 460 may include a plurality of mounting holes (not shown) configured to align with the plurality of apertures 162 formed in the mounting plate 164 of the mounting structure 160. The attachment mechanism 90, the mounting structure 160, and/or the mounting plate 164 may be securable to the transport pod 460 to facilitate translation of the attachment mechanism 90 and/or the endoscope 10 axially and/or longitudinally along the linear advancement device 450, the frame 452, and/or relative to the motorized introducer apparatus 200. In some embodiments, the mounting structure 160 may be configured to translate linearly along the frame 452 in response to operation of the motor 454 and/or the advancement mechanism 456.

In some embodiments, the surgical system 400 may include the motorized introducer apparatus 200 secured and/or fixedly attached to the frame 452 for translating the elongate shaft 30 of the endoscope 10 relative to a patient as the linear advancement device 450 translates the attachment mechanism 90 relative to the patient. For example, as the linear advancement device 450 translates the attachment mechanism 90 towards the patient, the motorized introducer apparatus 200 may advance the elongate shaft 30 of the endoscope 10 toward and/or into the patient. Similarly, as the linear advancement device 450 translates the attachment mechanism 90 away from the patient, the motorized introducer apparatus 200 may retract and/or withdraw the elongate shaft 30 of the endoscope 10 away from and/or out of the patient. In at least some embodiments, the surgical system 400 may be configured to operate the motorized introducer apparatus 200 in conjunction with and/or simultaneously with the linear advancement device 450 and/or the advancement mechanism 456.

In some embodiments, the linear advancement device 450 and/or the frame 452 may be securable and/or attachable relative to a surgical bed (not shown). In some embodiments, the linear advancement device 450 and/or the frame 452 may be removable when not in use. In some embodiments, the linear advancement device 450 and/or the frame 452 may be portable and/or configured to be moved between operating rooms. While illustrated in FIG. 31 with the motorized introducer apparatus 200 of FIG. 17, such illustration shall be understood to be merely exemplary and any motorized introducer apparatus 200 described herein may be usable with and/or may be attachable to the linear advancement device 450 and/or the frame 452.

As discussed herein, the attachment mechanism 90 and/or the second drive mechanism 180 may be configured to rotate the fixture 100 and/or the handle 20 and elongate shaft 30 of the endoscope 10 relative to the mounting structure 160 and/or the patient. The attachment mechanism 90 and/or the first drive mechanism 140 may be configured to engage the handle 20 of the endoscope 10 to operate the deflection mechanism 28 and/or to deflect the deflectable distal tip 32 of the elongate shaft 30. In some embodiments, the first drive mechanism 140 and the second drive mechanism 180 may be operatable independently of each other.

Figure 32:
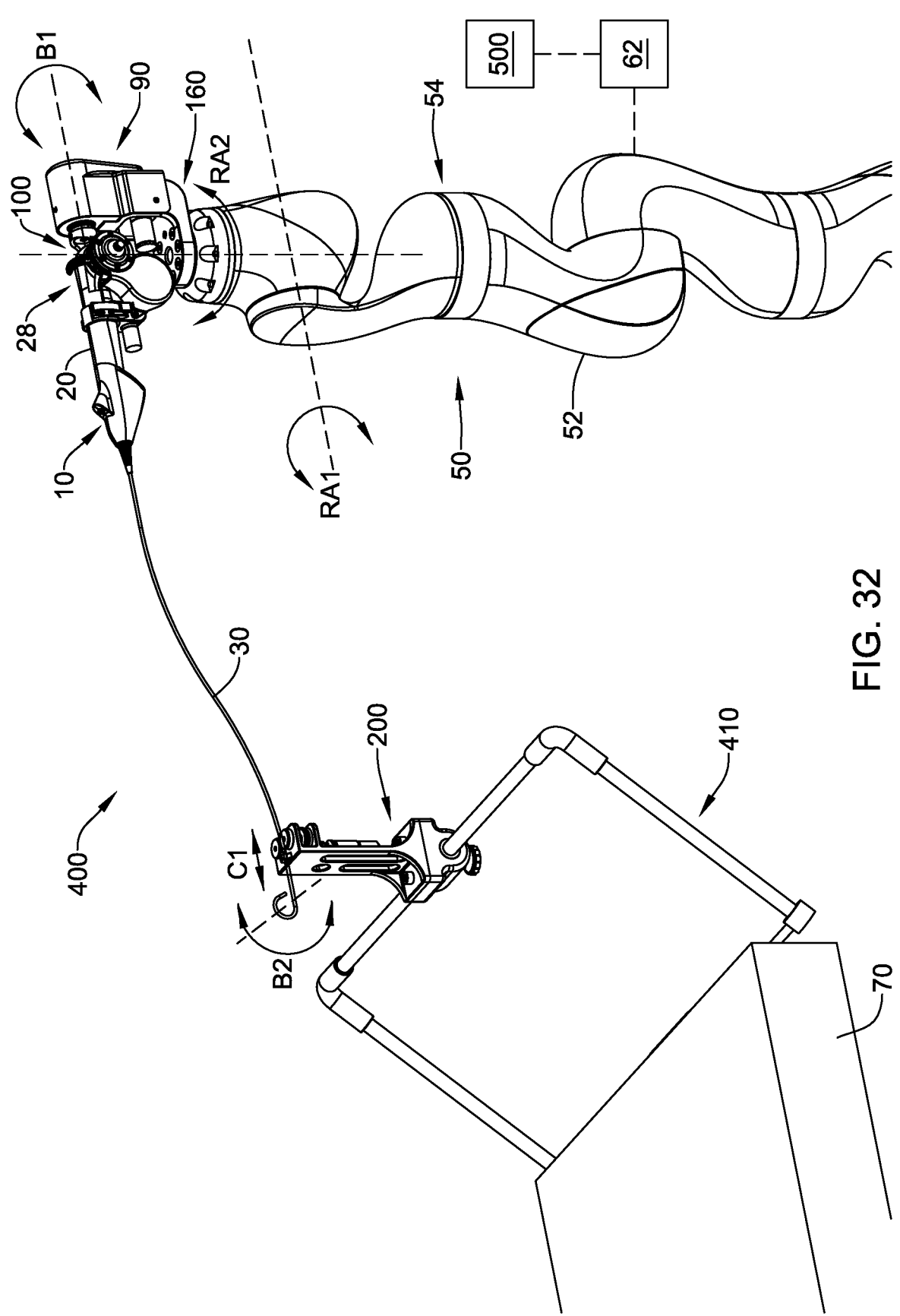
FIGS. 32-36 illustrate selected aspects of a surgical system for use with a surgical robot.
Figure 33:
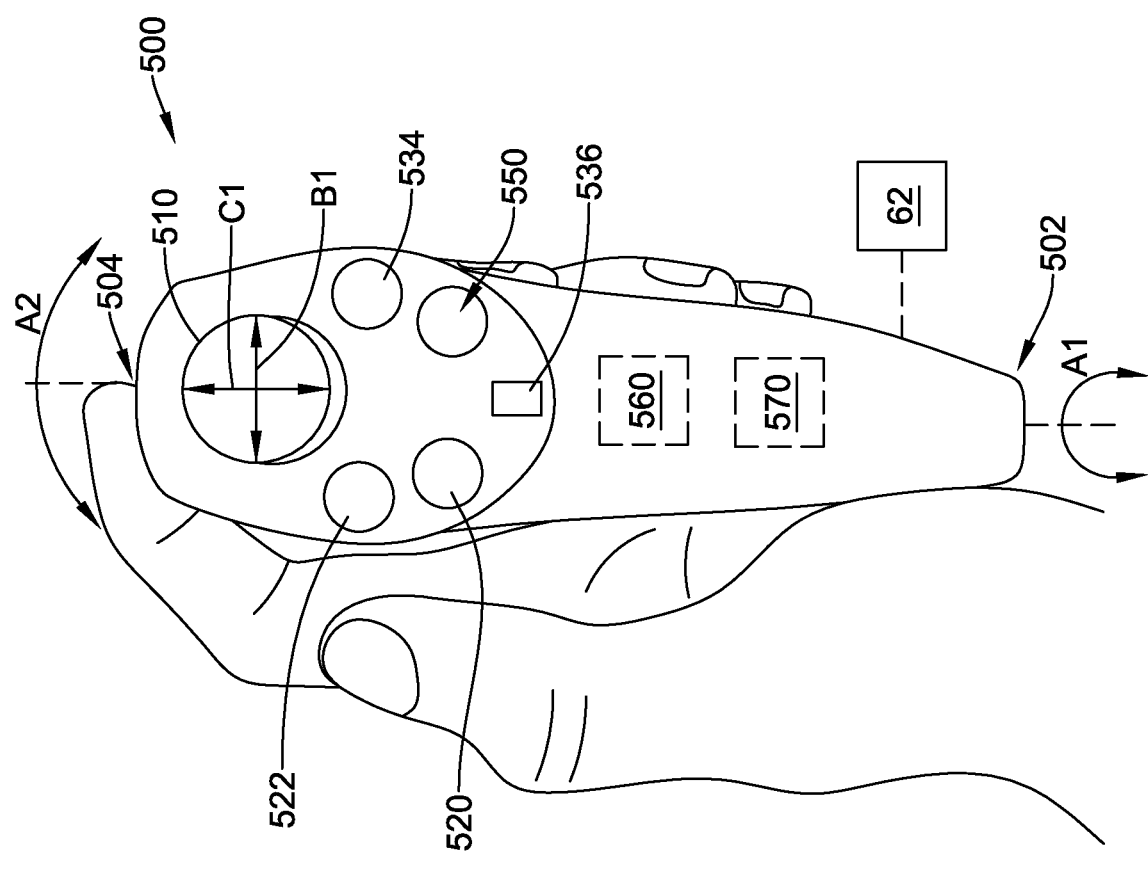
Figure 34:
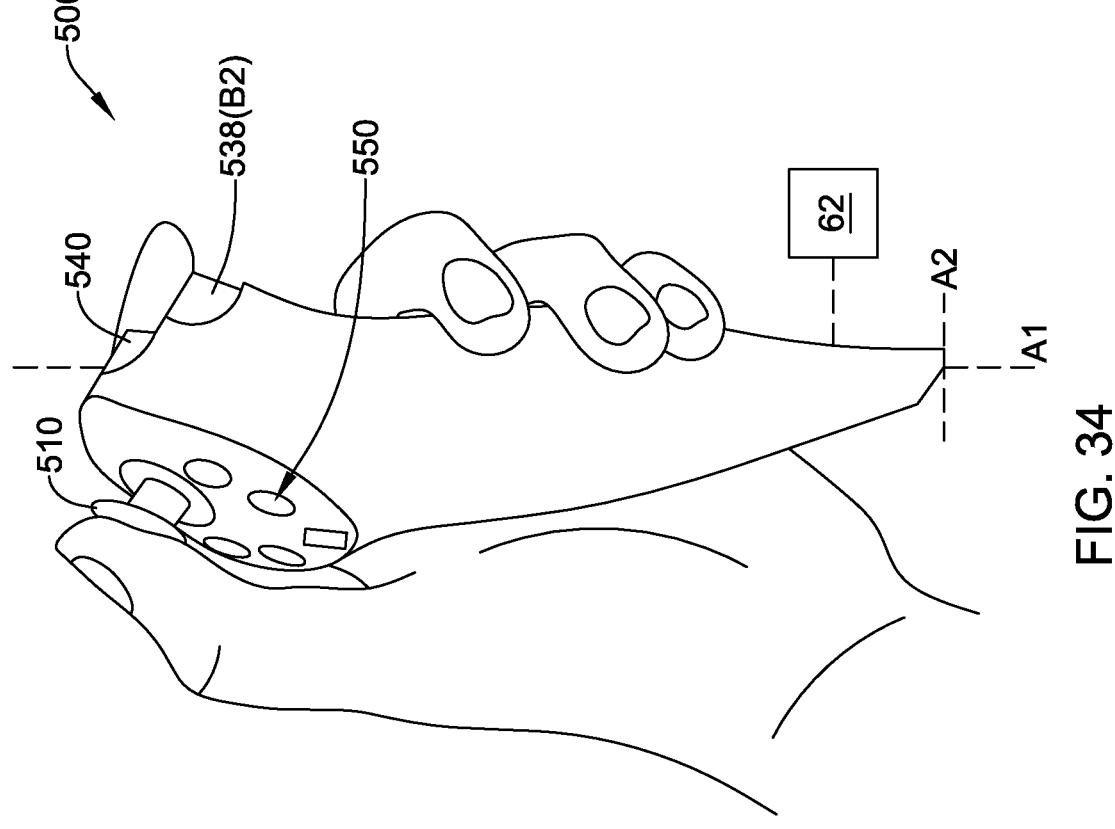

FIGS. 32-34 illustrate selected aspects of an example configuration of the surgical system 400 for use with the surgical robot 50. FIG. 32 illustrates selected movements of the surgical robot 50, the attachment mechanism 90, and/or the motorized introducer apparatus 200. FIGS. 33-34 illustrate selected corresponding features and/or motions of an input device 500. It shall be understood that any particular feature, button, label, etc. may be mixed and matched with any other feature, button, label, etc. described herein.

As shown schematically in FIG. 32, the surgical system 400 for use with the surgical robot 50 may include the endoscope 10 including the handle 20 and the elongate shaft 30 extending distally from the handle 20. The surgical system 400 may include the attachment mechanism 90 including the fixture 100 configured to receive the handle 20 of the endoscope 10 and the mounting structure 160 configured to attach the fixture 100 to the surgical robot 50 and/or the arm 52 of the surgical robot 50. The surgical system 400 may include the motorized introducer apparatus 200, as described herein, spaced apart from the surgical robot 50 and configured to translate the elongate shaft 30 of the endoscope 10 relative to the patient (not shown, but may be positioned on the surgical bed 70).

In at least some embodiments, the surgical system 400 may include an input device 500, selected aspects of which are shown in more detail in FIGS. 33-34, configured to be operated using one hand only. The input device 500 may be in electronic communication with the controller 62 for the surgical robot 50. In some embodiments, the input device 500 may be in wired communication with the controller 62. In some embodiments, the input device 500 may be in wireless communication with the controller 62. In some embodiments, the controller 62 may be integrated into the surgical robot 50 and the input device 500 may be in direct communication with the surgical robot 50. Other configurations are also contemplated. In some embodiments, the input device 500 may be configured to control motion and/or movement of the surgical robot 50, the arm 52 of the surgical robot 50, and/or the plurality of joints 54 of the surgical robot 50 and/or the motorized introducer apparatus 200 using one hand only.

The input device 500 may include a proximal end 502 and a distal end 504. Generally, the proximal end 502 may be disposed and/or positioned closer to the user's wrist than the distal end 504 when the input device 500 is being held by the one hand. In some embodiments, the input device 500 may include a plurality of motion sensors 560 configured to determine position and orientation of the input device 500 in space. In at least some embodiments, the plurality of motion sensors 560 may be disposed within the input device 500. The plurality of motion sensors 560 may be configured to sense and/or capture information related to pitch, roll, yaw, etc. of the input device 500 relative to a reference frame. In some embodiments, the input device 500 may include at least one feedback element 570 each operatively connected to a corresponding sensor (not shown) disposed at a distal tip and/or a distal end of the elongate shaft 30 of the endoscope 10. In some embodiments, the at least one feedback element 570 may include vibrations, audible signals, and/or visual signals. In some embodiments, the corresponding sensor(s) may include pressure sensors, temperature sensors, cameras and/or optical sensors, etc.

In some embodiments, the input device 500 may include a plurality of tactile buttons 550 operable using the one hand. In some embodiments, the plurality of tactile buttons 550 may be operable using a thumb of the one hand, one or more fingers of the one hand, and/or a combination of the thumb and the one or more fingers of the one hand. In some embodiments, the plurality of tactile buttons 550 may each be mapped to a specific function. FIGS. 33-34 illustrate some possible mappings for the plurality of tactile buttons 550. In shall be understood that other mappings are also contemplated. For example, some functions may be mapped to other buttons of the plurality of tactile buttons 550 and some additional or other functions may be mapped to the plurality of tactile buttons 550 described herein. The plurality of tactile buttons 550 may be flexible in their usage and mappings may be changed or varied based on user preference, procedure type, surgical robot capabilities, endoscope capabilities, etc.

In some embodiments, the plurality of tactile buttons 550 may include a set home button 520 and a go home button 522. The set home button 520 may be configured to set and/or store a home position of the surgical robot 50, the attachment mechanism 90, and/or the motorized introducer apparatus 200. The home position may be defined as a desired position and/or orientation of the surgical robot 50, the attachment mechanism 90, and/or the motorized introducer apparatus 200 and may be set by the user using the set home button 520. The go home button 522 may be configured to return the surgical robot 50, the attachment mechanism 90, and/or the motorized introducer apparatus 200 to the home position on demand. In some embodiments, the surgical robot 50, the attachment mechanism 90, and/or the motorized introducer apparatus 200 may move to a pre-defined start-up position and orientation. The predefined start-up position and orientation may be and/or may define the home position until or unless the home position is redefined by the user via the set home button 520. For example, after start-up of the surgical system 400, the user may reposition the surgical robot 50, the attachment mechanism 90, and/or the motorized introducer apparatus 200 to a second position and orientation, and then press the set home button 520 to redefine the home position to the second position. In some embodiments, once the set home button 520 has been used to define the home position or redefine the home position from the predefined start-up position, the home position may be fixed for the duration of the procedure. In some embodiments, the process of redefining the home position may be repeated as desired during the procedure. Other configurations are also contemplated.

In some embodiments, the plurality of tactile buttons 550 may include a calibration button 534. In some embodiments, the calibration button 534 may be configured to set a neutral reference frame for the orientation of the input device 500 wherein within the reference frame the input device 500 has zero roll, zero pitch, zero yaw, etc. After calibration, the reference frame will be used to sense and/or capture roll, pitch, yaw, etc. during the procedure. The user may use the calibration button 534 to save the orientation of the input device 500 relative to the reference frame. Thereafter, the plurality of motion sensors 560 and the reference frame will sense and/or capture the amount of commanded roll, pitch, yaw, etc. relative to the reference frame to control motion and/or movement of the surgical robot 50, the arm 52 of the surgical robot 50, and/or the plurality of joints 54 of the surgical robot 50.

In some embodiments, the plurality of tactile buttons 550 may include a clutch button 540. In some embodiments, the clutch button 540 may be configured as a safety guard and/or an on/off switch for movement of the surgical robot 50, the arm 52 of the surgical robot 50, and/or the plurality of joints 54 of the surgical robot 50. As such, the clutch button 540 may be configured to prevent unwanted movement of the surgical robot the arm 52 of the surgical robot 50, and/or the plurality of joints 54 of the surgical robot that may be caused by unintended and/or accidental movement of the input device 500 and/or unintended and/or accidental button presses of the plurality of tactile buttons 550. In some embodiments, movement of the input device 500 in space and/or relative to the reference frame while the clutch button 540 is depressed may control movement of the surgical robot 50, the arm 52 of the surgical robot 50, and/or the plurality of joints 54 of the surgical robot 50. In some embodiments, movement of the input device 500 in space and/or relative to the reference frame while the clutch button 540 is depressed may control movement of at least some joints of the surgical robot 50. In some embodiments, movement of the surgical robot 50, the arm 52 of the surgical robot 50, and/or the plurality of joints 54 of the surgical robot 50 may be prevented when the clutch button 540 is released. Accordingly, for the user to command a specific motion or movement, the clutch button 540 should always be pressed during the motion command (e.g., movement of the input device in space and/or depressing one or more of the plurality of tactile buttons). As soon as the clutch button 540 is released, all motion and/or movement of the surgical robot 50, the arm 52 of the surgical robot 50, and/or the plurality of joints 54 of the surgical robot 50 will stop and the surgical robot 50, the arm 52 of the surgical robot 50, and/or the plurality of joints 54 of the surgical robot 50 at will be held in its last received position and orientation and waits until the clutch button 540 is depressed again to resume motion and/or movement.

In some embodiments, the plurality of tactile buttons 550 may include a speed mode button 536. In some embodiments, operational speed of the surgical robot 50, the arm 52 of the surgical robot 50, and/or the plurality of joints 54 of the surgical robot 50 may be controllable and/or adjustable using the speed mode button 536. In some embodiments, the speed mode button 536 may be configured to cycle through a plurality of speed modes including but not limited to extra slow, slow, normal, fast, extra fast, etc. In some embodiments, the speed mode button 536 may be configured to change operational speed of the surgical robot 50, the arm 52 of the surgical robot 50, and/or the plurality of joints 54 of the surgical robot 50 when moving from a known configuration to a commanded configuration. In some embodiments, a surgical procedure may have some and/or selected phases where fine and/or small motions, or alternatively fast and/or large motions, of the surgical robot 50 are required. In some embodiments, the speed mode button 536 may be configured to change between different mappings and/or mapping scaling between the controller 62 and the surgical robot 50 to achieve the desired operational speed of the surgical robot 50, the arm 52 of the surgical robot 50, and/or the plurality of joints 54 of the surgical robot 50.

In some embodiments, the plurality of tactile buttons 550 may include one or more additional buttons that are not explicitly illustrated. As discussed herein, in some embodiments, some of the plurality of tactile buttons 550 may be mapped differently. In some embodiments, the plurality of tactile buttons 550 may include at least one of the following: an irrigation button configured to activate fluid irrigation through the endoscope 10, an image capture button configured to capture an image seen via a camera disposed within the endoscope 10, and a memory button configured to save a second stored position of the surgical robot 50, the arm 52 of the surgical robot 50, and/or the plurality of joints 54 of the surgical robot 50 that of the surgical robot 50, the arm 52 of the surgical robot 20, and/or the plurality of joints 54 of the surgical robot 50 may currently be positioned and/or oriented in (e.g., a current position). In some embodiments, the second stored position of the surgical robot 50, the arm 52 of the surgical robot 50, and/or the plurality of joints 54 of the surgical robot 50 may be saved in addition to the home position. In some embodiments, depressing the memory button a second time may instruct the surgical robot 50, the arm 52 of the surgical robot 50, and/or the plurality of joints 54 of the surgical robot 50 to return to the second stored position (e.g., the position that was saved using the memory button). Other configurations, additional buttons, and/or mapped functions are also contemplated.

In some embodiments, the plurality of tactile buttons 550 may include a deflection button 538 configured to control the first motor 130 and/or the first drive mechanism 140 to thereby control the deflection mechanism 28 of the endoscope 10 to operate the deflectable distal tip 32 about axis B2. In some embodiments, an amount of depression of the deflection button 538 may correspond to an amount of deflection of the deflectable distal tip 32 about axis B2. For example, depressing the deflection button 538 about 50% may deflect the deflectable distal tip 32 about 50% of its movable range. Similarly, depressing the deflection button 538 about 25% may deflect the deflectable distal tip 32 about 25% of its movable range, depressing the deflection button 538 about 75% may deflect the deflectable distal tip 32 about 75% of its movable range, depressing the deflection button 538 100% may deflect the deflectable distal tip 32 100% of its movable range, etc. In some embodiments, releasing the deflection button 538 may hold the deflectable distal tip 32 at its then-current amount of deflection. In some embodiments, a different command may be given to release or reverse movement of the deflection mechanism 28 and/or permit the deflectable distal tip 32 to return to a neutral configuration (e.g., a straight configuration). In some embodiments, a double press on the deflection button 538 may be configured to release or reverse movement of the deflection mechanism 28 and/or permit the deflectable distal tip 32 to return to the neutral configuration (e.g., the straight configuration).

In some embodiments, the plurality of tactile buttons 550 may include two deflection buttons configured to control the first motor 130 and/or the first drive mechanism 140 to thereby control the deflection mechanism 28 of the endoscope 10 to operate the deflectable distal tip 32 about axis B2, wherein each deflection button controls a different direction of deflection. For example, a first deflection button may be configured to deflect the deflectable distal tip 32 in a clockwise direction about axis B2 and a second deflection button may be configured to deflect the deflectable distal tip 32 in a counterclockwise direction about axis B2. Other configurations are also contemplated.

In some embodiments, the input device 500 may include a joystick 510 configured for operation by the thumb of the one hand. In some embodiments, the joystick 510 may be configured to control the second motor 170 of the attachment mechanism 90. In some embodiments, movement of the joystick 510 left and right may control operation of the second motor 170 and/or the second drive mechanism 180 to rotate the fixture 100 and/or the handle 20 disposed therein relative to the mounting structure 160 about axis B1. For example, movement of the joystick 510 to the left may command the second motor 170 and/or the second drive mechanism 180 to rotate the fixture 100 and/or the handle 20 disposed therein counterclockwise about axis B1, as viewed from the mounting structure 160 towards the deflectable distal tip 32 of the elongate shaft 30 of the endoscope 10, and movement of the joystick 510 to the right may command the second motor 170 and/or the second drive mechanism 180 to rotate the fixture 100 and/or the handle 20 disposed therein clockwise about axis B1, as viewed from the mounting structure 160 towards the deflectable distal tip 32 of the elongate shaft 30 of the endoscope 10. Other configurations are also contemplated.

In some embodiments, the joystick 510 may be configured to control the motor 220 and/or the motorized introducer apparatus 200. In some embodiments, movement of the joystick 510 proximally (e.g., towards the proximal end 502 of the input device 500) and distally (e.g., towards the distal end 504 of the input device 500) may control operation of the motor 220 and/or the motorized introducer apparatus 200 to translate the elongate shaft 30 of the endoscope 10 relative to the patient and/or through the motorized introducer apparatus 200 along axis Cl and/or the axis of movement 202 (e.g., FIG. 17). For example, movement of the joystick 510 proximally (e.g., towards the proximal end 502 of the input device 500) may translate the elongate shaft 30 of the endoscope 10 proximally relative to the patient and/or through the motorized introducer apparatus 200, and movement of the joystick 510 distally (e.g., towards the distal end 504 of the input device 500) may translate the elongate shaft 30 of the endoscope 10 distally relative to the patient and/or through the motorized introducer apparatus 200. In some embodiments, movement of the joystick 510 proximally (e.g., towards the proximal end 502 of the input device 500) may withdraw and/or retract the elongate shaft 30 of the endoscope 10 away from and/or out of the patient. In some embodiments, movement of the joystick 510 distally (e.g., towards the distal end 504 of the input device 500) may advance the elongate shaft 30 of the endoscope 10 towards and/or into the patient.

In some embodiments, the clutch button 540 may also be configured to prevent unwanted movement of the motorized introducer apparatus 200 in place of or in addition to preventing unwanted movement of the surgical robot 50, the arm 52 of the surgical robot 50, and/or the plurality of joints 54 of the surgical robot 50. As such, in some embodiments, the user may need to depress the clutch button 540 in order to operate the motorized introducer apparatus 200.

In some embodiments, the plurality of motion sensors 560 may be mapped to and/or may control selected aspects of the surgical robot 50, such as selected joints of the plurality of joints 54 of the surgical robot 50. In some embodiments, the input device 500 and the plurality of motion sensors 560 may be configured to send commands to the controller 62 permitting and/or promoting smooth and/or dynamic movement of the surgical robot 50, the arm 52 of the surgical robot 50, and/or the plurality of joints 54 of the surgical robot 50.

In some embodiments, movement of the input device 500 about a first axis A1 while the clutch button 540 is depressed may cause movement of a first joint of the plurality of joints 54 of the surgical robot 50 about a first robot axis RA1. In some embodiments, the first axis A1 may extend generally from the proximal end 502 to the distal end 504 of the input device 500 and the plurality of motion sensors 560 may be configured to sense and/or measure roll of the input device 500 about the first axis A1. As such, as the input device 500 is rolled or rotated about the first axis A1, the first joint of the plurality of joints 54 of the surgical robot 50 may rotate about the first robot axis RA1. In some embodiments, movement of the input device 500 about a second axis A2 while the clutch button 540 is depressed may cause movement of a second joint of the plurality of joints 54 of the surgical robot 50 about a second robot axis RA2. In some embodiments, the second axis A2 may extend generally perpendicular to the first axis A1 and the plurality of motion sensors 560 may be configured to sense and/or measure yaw of the input device 500 about the second axis A2. As such, as the input device 500 is yawed or rotated about the second axis A2, the second joint of the plurality of joints 54 of the surgical robot 50 may rotate about the second robot axis RA2. In some embodiments, movement of the input device 500 about a third axis (not shown) while the clutch button 540 is depressed may cause movement of a third joint of the plurality of joints 54 of the surgical robot 50 about a third robot axis (not shown). In some embodiments, the third axis may extend generally perpendicular to the first axis A1 and the second axis A2 and may sense and/or measure pitch of the input device 500. As such, as the input device 500 is pitched or rotated about the third axis, the third joint of the plurality of joints 54 of the surgical robot 50 may rotate about the third robot axis. Other configurations are also contemplated. For example, the plurality of motion sensors 560 may be configured to sense and/or measure pitch about the second axis A2 instead of yaw, etc.

Figure 35:
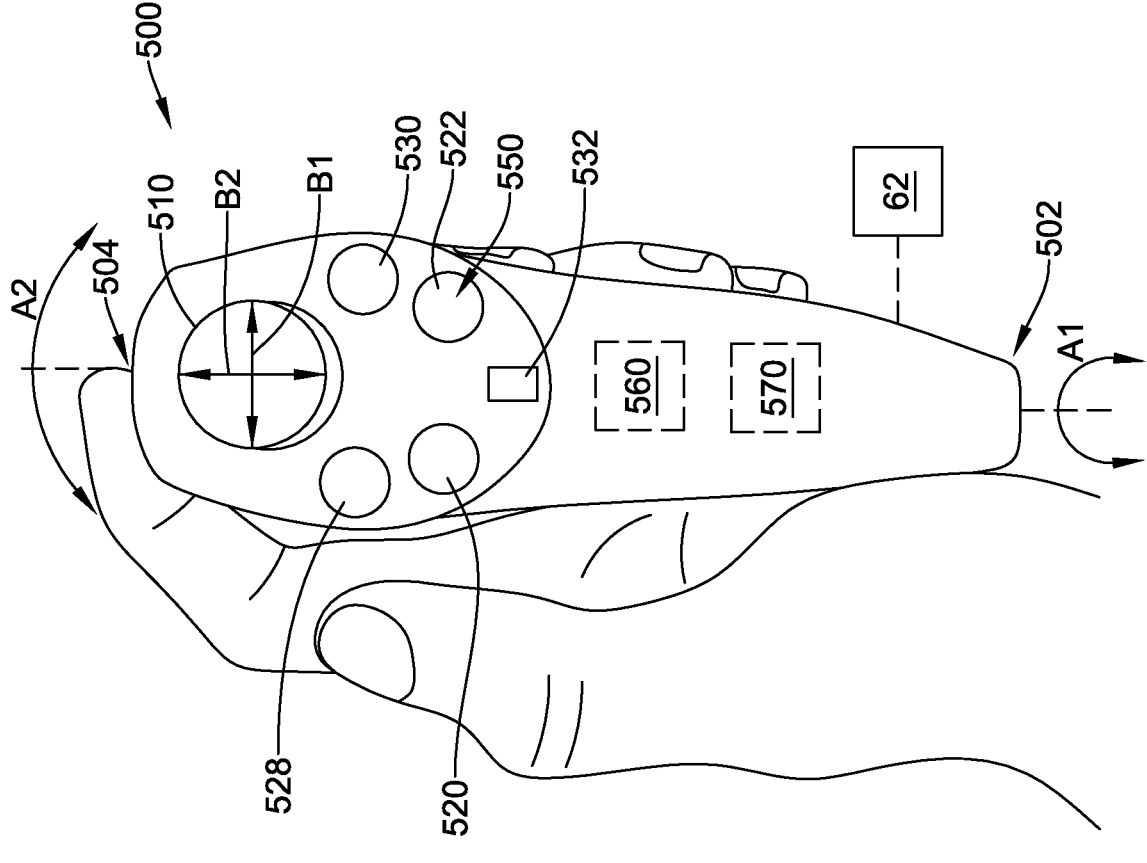
Figure 36:
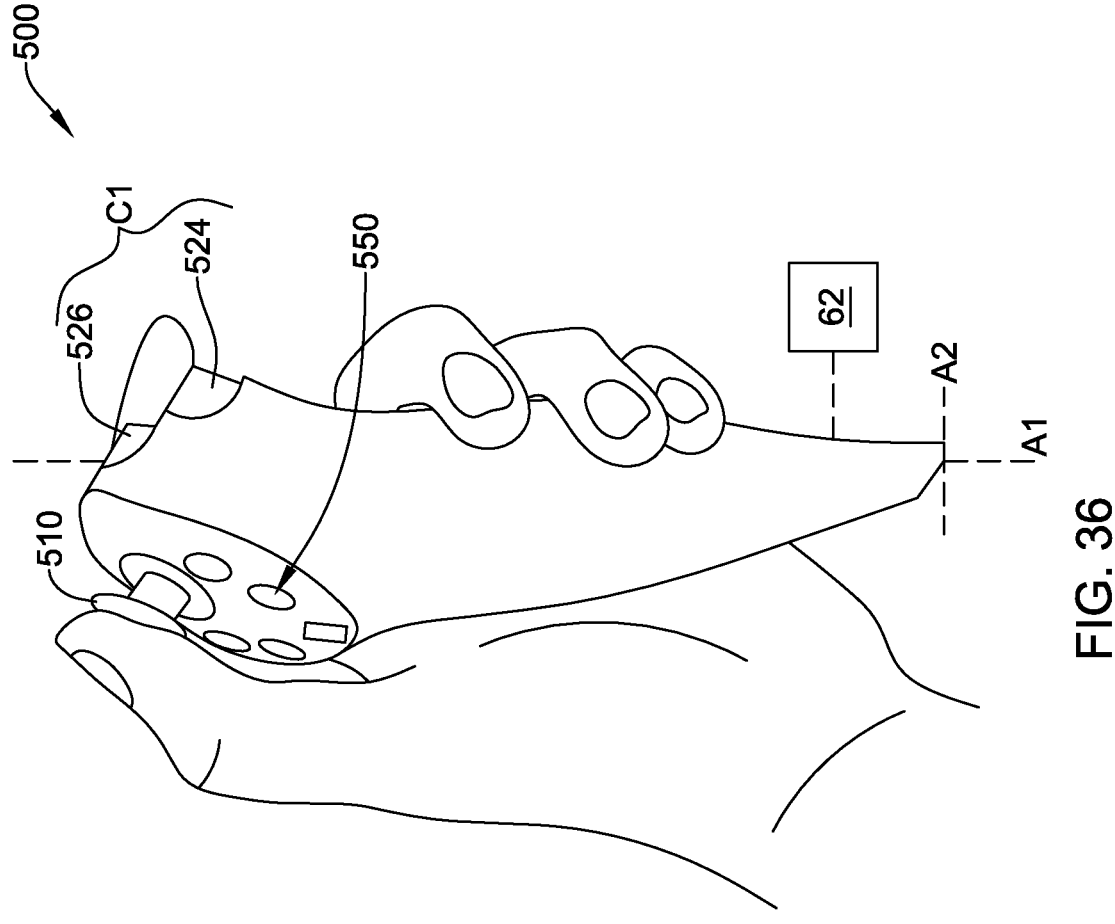

FIGS. 35-36 illustrate selected corresponding features and/or motions of the input device 500 and may refer back to selected movements of the surgical robot 50, the attachment mechanism 90, and/or the motorized introducer apparatus 200 shown in FIG. 32. Without limitation, FIGS. 35-36 illustrate some alternative mappings for the plurality of tactile buttons 550 and/or the joystick 510 of the input device 500. As discussed herein, different functions and/or movements may be mapped to the input device 500 differently depending on user preference, procedure type, etc.

In some embodiments, the plurality of tactile buttons 550 may include a lock mode button 528 configured to lock the surgical robot 50 and/or the attachment mechanism 90 is their current configuration, position, and/or orientation. After activation of and/or depressing the lock mode button 528, the surgical robot 50 and/or the attachment mechanism 90 and its attached motors and drive mechanisms are prevented from moving. Movement of the input device 500 does not result in corresponding movement of the surgical robot 50 and/or the attachment mechanism 90 and its attached motors and drive mechanisms when lock mode is enabled. This may allow for a stable system which is not prone to movement or deviation when performing tasks in situ such as dusting, basketing of stones, etc.

In some embodiments, the plurality of tactile buttons 550 may include an operational mode button 530 configured to permit all movement functionality of the surgical robot 50 and/or the attachment mechanism 90. Depressing and/or activating the operational mode button 530 effectively deactivates and/or counteracts the lock mode button 528. After activation of and/or depressing the operational mode button 530, the surgical robot 50 and/or the attachment mechanism 90 and its attached motors and drive mechanisms are permitted to move and/or operate. Movement of the input device 500 results in corresponding movement of the surgical robot 50 and/or the attachment mechanism 90 and its attached motors and drive mechanisms when the operational mode is enabled.

In some embodiments, the plurality of tactile buttons 550 may include a manual positioning mode button 532 configured to permit manual movement of the surgical robot 50, the arm 52 of the surgical robot 50, and/or the plurality of joints 54 of the surgical robot 50 and/or the attachment mechanism 90 without any other input from the input device 500. After activation of and/or depressing the manual positioning mode button 532, the surgical robot 50, the arm 52 of the surgical robot 50, and/or the plurality of joints 54 of the surgical robot 50 and/or the attachment mechanism 90 and its attached motors and drive mechanisms may be manually moved and/or repositioned by the user and/or some other person. In one example, manual positioning mode may be useful for positioning and/or orienting the surgical robot 50, the arm 52 of the surgical robot 50, and/or the plurality of joints 54 of the surgical robot 50 in a desired position for calibration, or for saving the second stored position of the surgical robot 50, the arm 52 of the surgical robot 50, and/or the plurality of joints 54 of the surgical robot 50. In another example, manual positioning mode may be useful for manually positioning and/or orienting the endoscope 10, the handle 20, and/or the elongate shaft 30 in a desired position relative to the patient.

In some embodiments, the plurality of tactile buttons 550 may include an extend button 524 configured to advance the elongate shaft 30 of the endoscope 10 through the motorized introducer apparatus 200 along axis C1 and/or the axis of movement 202 (e.g., FIG. 17). In some embodiments, the extend button 524 may be configured to operate the motor 220 of the motorized introducer apparatus 200 to advance the elongate shaft 30 of the endoscope 10 through the motorized introducer apparatus 200 and/or towards the patient.

In some embodiments, the plurality of tactile buttons 550 may include a retract button 526 configured to retract the elongate shaft 30 of the endoscope 10 through the motorized introducer apparatus 200 along axis C1 and/or the axis of movement 202 (e.g., FIG. 17). In some embodiments, the retract button 526 may be configured to operate the motor 220 of the motorized introducer apparatus 200 to retract the elongate shaft 30 of the endoscope 10 through the motorized introducer apparatus 200 and/or away from the patient.

In some embodiments, the joystick 510 may be configured to control the first motor 130 of the attachment mechanism 90. In some embodiments, movement of the joystick 510 proximally (e.g., towards the proximal end 502 of the input device 500) and distally (e.g., towards the distal end 504 of the input device 500) may control operation of the first motor 130 and/or the first drive mechanism 140 to operate the deflection mechanism 28 and deflect the deflectable distal tip 32 of the elongate shaft 30 of the endoscope 10. For example, movement of the joystick 510 proximally (e.g., towards the proximal end 502 of the input device 500) may deflect the deflectable distal tip 32 of the elongate shaft 30 of the endoscope 10 in a first direction (e.g., upwards) about axis B2 and/or relative to the longitudinal axis 12 (e.g., FIG. 1), and movement of the joystick 510 distally (e.g., towards the distal end 504 of the input device 500) may deflect the deflectable distal tip 32 of the elongate shaft 30 of the endoscope 10 in a second direction opposite the first direction (e.g., downwards) about axis B2 and/or relative to the longitudinal axis 12 (e.g., FIG. 1), or vice versa.

In some embodiments, the joystick 510 may be configured to control the second motor 170 of the attachment mechanism 90. In some embodiments, movement of the joystick 510 left and right may control operation of the second motor 170 and/or the second drive mechanism 180 to rotate the fixture 100 and/or the handle 20 disposed therein relative to the mounting structure 160 about axis B1. For example, movement of the joystick 510 to the left may command the second motor 170 and/or the second drive mechanism 180 to rotate the fixture 100 and/or the handle 20 disposed therein counterclockwise about axis B1, as viewed from the mounting structure 160 towards the deflectable distal tip 32 of the elongate shaft 30 of the endoscope 10, and movement of the joystick 510 to the right may command the second motor 170 and/or the second drive mechanism 180 to rotate the fixture 100 and/or the handle 20 disposed therein clockwise about axis B1, as viewed from the mounting structure 160 towards the deflectable distal tip 32 of the elongate shaft 30 of the endoscope 10. Other configurations are also contemplated.

Other configurations and/or mappings for the input device 500, the joystick 510, and/or the plurality of tactile buttons 550, including but not limited to combinations of the configurations and/or mappings disclosed herein, are also contemplated. In some embodiments, the joystick 510 and/or the plurality of tactile buttons 550, and/or various combinations thereof, may direct movements of the surgical robot 50 without using input from any of the plurality of motion sensors 560 (e.g., movement of the input device 500 in space has no effect upon the surgical robot 50). Accordingly, in some embodiments, the input device 500 may be devoid of the plurality of motion sensors 560 while still being configured to control multiple axes and/or degrees of motion of the surgical robot 50, the arm 52 of the surgical robot 50, the plurality of joints 54 of the surgical robot 50, and/or the motorized introducer apparatus 200.

The materials that can be used for the various components of the system and the various elements thereof disclosed herein may include those commonly associated with medical devices. For simplicity purposes, the following discussion refers to the system. However, this is not intended to limit the system, devices, and/or methods described herein, as the discussion may be applied to other elements, members, components, or devices disclosed herein, such as, but not limited to, the attachment mechanism, the fixture, the motorized introducer apparatus, the support frame, the input device, etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable polymers may include poly-tetrafluoroethylene (PTFE), ethylene tetrafluoroethylene (ETFE), fluorinated ethylene propylene (FEP), polyoxymethylene (POM, for example, DELRIN®), polyether block ester, polyurethane (for example, Polyurethane 85A), polypropylene (PP), polyvinylchloride (PVC), polyether-ester (for example, ARNITEL®), ether or ester based copolymers (for example, butylene/poly(alkylene ether) phthalate and/or other polyester elastomers such as HYTREL®), polyamide (for example, DURETHAN® or CRISTAMID®), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID®), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, Elast-Eon® or ChronoSil®), biocompatible polymers, other suitable materials, or mixtures, combinations, copolymers thereof, polymer/metal composites, and the like. In some embodiments, the system and/or components thereof can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®), other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-protein and/or anti-bacterial agents (such as 2-methacryloyloxyethyl phosphorylcholine (MPC) and its polymers or copolymers); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A surgical system for use with a surgical robot, comprising:
   an endoscope including a handle and an elongate shaft extending distally from the handle;
   an attachment mechanism including a fixture configured to receive the handle of the endoscope and a mounting structure configured to attach the fixture to the surgical robot;
   a motorized introducer apparatus spaced apart from the surgical robot and configured to translate the elongate shaft of the endoscope relative to a patient; and
   an input device configured to be operated using one hand only, the input device including:
      a plurality of tactile buttons operable using the one hand; and
      a joystick configured for operation by a thumb of the one hand.

2. The surgical system of claim 1, wherein the plurality of tactile buttons includes a set home button and a go home button.

3. The surgical system of claim 1, wherein the plurality of tactile buttons includes:

an extend button configured to advance the shaft of the endoscope through the motorized introducer apparatus; and a retract button configured to retract the shaft of the endoscope through the motorized introducer apparatus.

4. The surgical system of claim 1, wherein the plurality of tactile buttons includes a lock mode button configured to lock the surgical robot and the attachment mechanism in their current configuration.

5. The surgical system of claim 1, wherein the plurality of tactile buttons includes an operational mode button configured to permit all movement functionality of the surgical robot and the attachment mechanism.

6. The surgical system of claim 1, wherein the fixture includes a first motor operably coupled to a first drive mechanism, the first drive mechanism being configured to engage the handle of the endoscope to operate a deflection mechanism of the endoscope; and wherein the mounting structure includes a second motor operably coupled to a second drive mechanism, the second drive mechanism being configured to rotate the fixture relative to the mounting structure.

7. The surgical system of claim 6, wherein the joystick is configured to control the first motor and the second motor.

8. The surgical system of claim 1, wherein the plurality of tactile buttons includes a manual positioning mode button configured to permit manual movement of the surgical robot without any other input from the input device.

9. The surgical system of claim 1, wherein the input device includes at least one feedback element each operatively connected to a corresponding sensor disposed at a distal tip of the elongate shaft of the endoscope.

10. A surgical system for use with a surgical robot, comprising:

an endoscope including a handle and an elongate shaft extending distally from the handle;

an attachment mechanism including a fixture configured to receive the handle of the endoscope and a mounting structure configured to attach the fixture to the surgical robot;

a motorized introducer apparatus spaced apart from the surgical robot and configured to translate the elongate shaft of the endoscope relative to a patient; and an input device configured to be operated using one hand only, the input device including:

a plurality of tactile buttons operable using the one hand, the plurality of tactile buttons including a clutch button;

a joystick configured for operation by a thumb of the one hand; and a plurality of motion sensors configured to determine position and orientation of the input device in space;

wherein movement of the input device in space while the clutch button is depressed controls movement of at least some joints of the surgical robot;

wherein movement of the surgical robot is prevented when the clutch button is released.

11. The surgical system of claim 10, wherein the plurality of tactile buttons includes a set home button and a go home button.

12. The surgical system of claim 10, wherein the plurality of tactile buttons includes a calibration button.

13. The surgical system of claim 10, wherein the plurality of tactile buttons includes a speed mode button.

14. The surgical system of claim 10, wherein the plurality of tactile buttons includes at least one of the following:

an irrigation button configured to activate fluid irrigation through the endoscope, an image capture button configured to capture an image seen via a camera disposed within the endoscope, and a memory button configured to save a second stored position of the surgical robot.

15. The surgical system of claim 10, wherein the fixture includes a first motor operably coupled to a first drive mechanism, the first drive mechanism being configured to engage the handle of the endoscope to operate a deflection mechanism of the endoscope; and wherein the mounting structure includes a second motor operably coupled to a second drive mechanism, the second drive mechanism being configured to rotate the fixture relative to the mounting structure.

16. The surgical system of claim 15, wherein the joystick is configured to control the second motor and the motorized introducer apparatus.

17. The surgical system of claim 15, wherein the plurality of tactile buttons includes a deflection button configured to control the first motor.

18. The surgical system of claim 10, wherein movement of the input device about a first axis while the clutch button is depressed causes movement of a first joint of the surgical robot about a first robot axis.

19. The surgical system of claim 10, wherein movement of the input device about a second axis while the clutch button is depressed causes movement of a second joint of the surgical robot about a second robot axis.

20. A surgical system for use with a surgical robot, comprising:

an endoscope including a handle and an elongate shaft extending distally from the handle;

an attachment mechanism including a fixture configured to receive the handle of the endoscope and a mounting structure configured to attach the fixture to the surgical robot;

a motorized introducer apparatus spaced apart from the surgical robot and configured to translate the elongate shaft of the endoscope relative to a patient; and an input device configured to control motion of the surgical robot and/or the motorized introducer apparatus using one hand only, the input device including:

a plurality of tactile buttons operable using the one hand; and a joystick configured for operation by a thumb of the one hand.

* * * * *